(12) United States Patent
Zhai et al.

(10) Patent No.: US 10,845,443 B2
(45) Date of Patent: *Nov. 24, 2020

(54) SYSTEM AND METHOD FOR MAGNETIC RESONANCE IMAGING RECONSTRUCTION USING NOVEL K-SPACE SAMPLING SEQUENCES

(71) Applicant: SHANGHAI UNITED IMAGING HEALTHCARE CO., LTD., Shanghai (CN)

(72) Inventors: Renkuan Zhai, Shanghai (CN); Guobin Li, Shanghai (CN); Chaohong Wang, Shanghai (CN); Zhaopeng Li, Shanghai (CN); Weiguo Zhang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/508,428

(22) Filed: Jul. 11, 2019

(65) Prior Publication Data

US 2019/0369187 A1    Dec. 5, 2019

Related U.S. Application Data

(63) Continuation of application No. 15/314,476, filed as application No. PCT/CN2016/085412 on Jun. 12, 2016, now Pat. No. 10,353,035.

(30) Foreign Application Priority Data

Jul. 23, 2015   (CN) .......................... 2015 1 0437221
Oct. 29, 2015   (CN) .......................... 2015 1 0719200

(51) Int. Cl.
*G01R 33/48*     (2006.01)
*A61B 5/055*     (2006.01)
(Continued)

(52) U.S. Cl.
CPC .......... *G01R 33/4818* (2013.01); *A61B 5/055* (2013.01); *A61B 5/7207* (2013.01);
(Continued)

(58) Field of Classification Search
CPC combination set(s) only.
See application file for complete search history.

(56) References Cited

U.S. PATENT DOCUMENTS 5,561,370 A   10/1996 Fuderer
5,570,019 A   10/1996 Moonen et al.
(Continued)

FOREIGN PATENT DOCUMENTS

CN    104181487 A    12/2014
CN    104569882 A    4/2015
(Continued)

OTHER PUBLICATIONS

International Search Report in PCT/CN2016/085412 dated Sep. 21, 2016, 5 pages.
(Continued)

*Primary Examiner* — Jay Patidar
(74) *Attorney, Agent, or Firm* — Metis IP LLC

(57) ABSTRACT

A system and method for magnetic resonance imaging reconstruction using novel k-space sampling sequences is provided. The method includes dividing k-space into a plurality of regions along a dividing direction; scanning an object using a plurality of sampling sequences; acquiring a plurality of groups of data lines; filling the plurality of
(Continued)

groups of data lines into the plurality of regions of the k-space; and reconstructing an image based on the filled k-space.

20 Claims, 16 Drawing Sheets

(51) Int. Cl.
*G01R 33/561* (2006.01)
*G01R 33/565* (2006.01)
*A61B 5/00* (2006.01)
*G01R 33/56* (2006.01)

(52) U.S. Cl.
CPC ....... *G01R 33/482* (2013.01); *G01R 33/4824* (2013.01); *G01R 33/565* (2013.01); *G01R 33/5616* (2013.01); *G01R 33/5617* (2013.01); *G01R 33/56545* (2013.01); *A61B 5/742* (2013.01); *G01R 33/5607* (2013.01); *G01R 33/56509* (2013.01); *G01R 33/56527* (2013.01)

(56) References Cited

U.S. PATENT DOCUMENTS

| 5,742,163 | A | 4/1998 | Liu et al. |
| 5,825,185 | A | 10/1998 | Liu et al. |
| 6,369,568 | B1 | 4/2002 | Ma et al. |
| 6,414,487 | B1 | 7/2002 | Anand et al. |
| 6,420,870 | B1 | 7/2002 | Kiefer |
| 7,860,291 | B2 | 12/2010 | Hwang |
| 8,417,005 | B1 | 4/2013 | Martel et al. |
| 9,103,898 | B2 | 8/2015 | Holmes et al. |
| 2004/0027124 | A1* | 2/2004 | Abe ................ A61B 5/055 324/306 |
| 2012/0313641 | A1 | 12/2012 | Labadie et al. |
| 2015/0073263 | A1 | 3/2015 | Gdaniec et al. |
| 2015/0091570 | A1 | 4/2015 | Gross et al. |
| 2015/0091572 | A1 | 4/2015 | Gross et al. |
| 2015/0301136 | A1 | 10/2015 | Li et al. |

FOREIGN PATENT DOCUMENTS

| EP | 2631664 A1 | 8/2013 |
| WO | 2015086415 A1 | 6/2015 |
| WO | 2015181091 A2 | 12/2015 |

OTHER PUBLICATIONS

Written Opinion in PCT/CN2016/085412 dated Sep. 21, 2016, 4 pages.

The Extended European Search Report in European Application No. 16827127.8 dated Jul. 19, 2018, 15 pages.

Julian R. MacLaren et al., A Modified View Ordering for Artifact Reduction in MRI, Proceeding of the 29th Annual International Conference of the IEEE EMBS, 2053-2056, 2007.

* cited by examiner

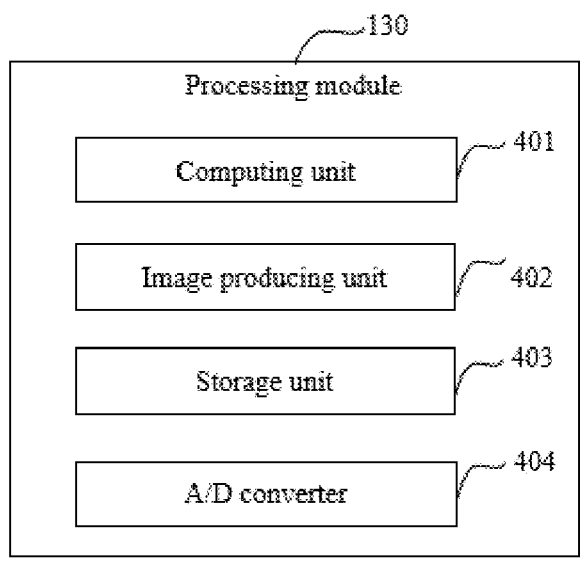
FIG. 4-A
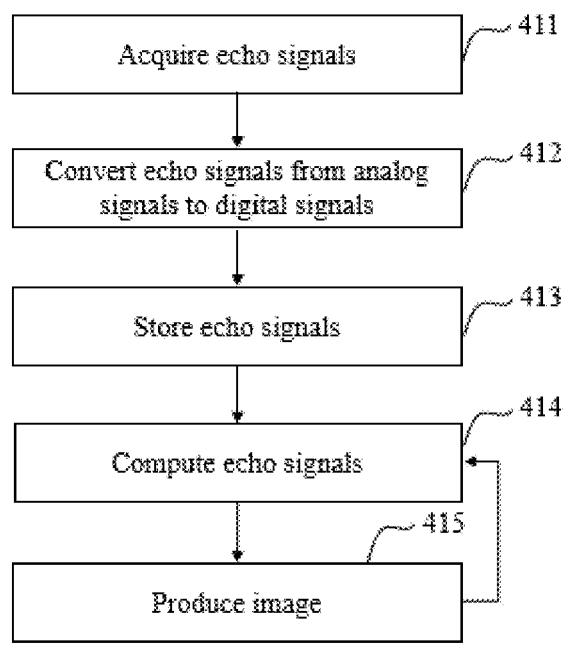
FIG. 4-B

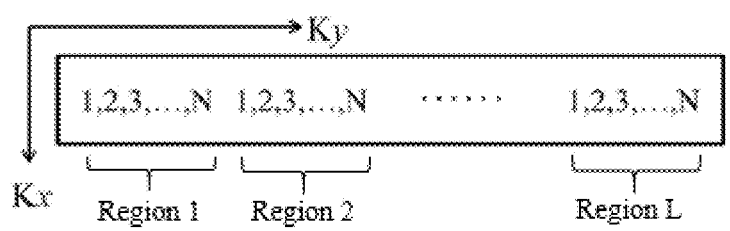
FIG. 8-A
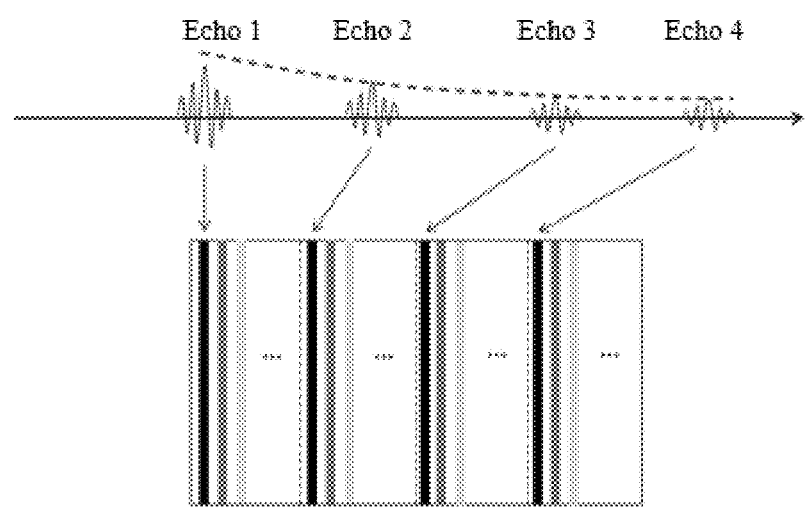
FIG. 8-B

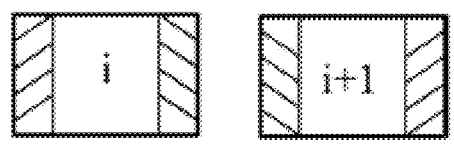
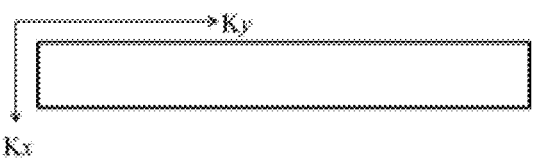
FIG. 9-A
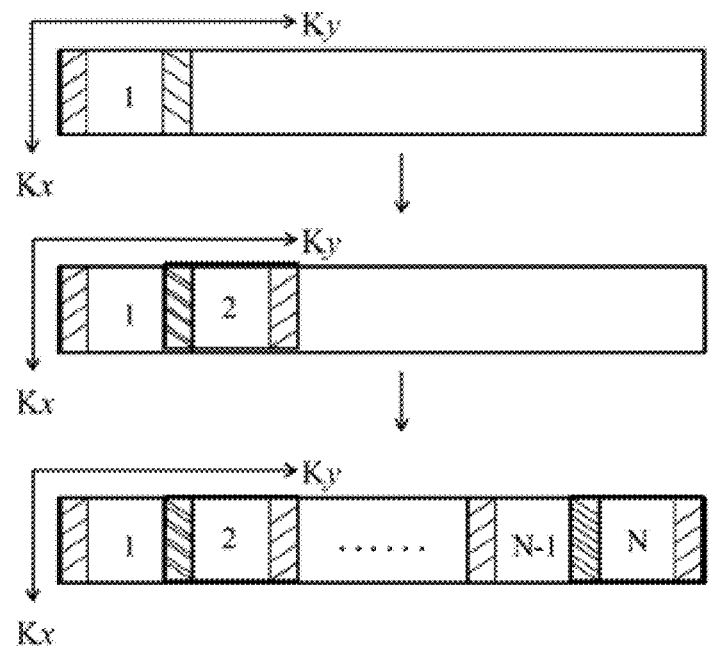
FIG. 9-B

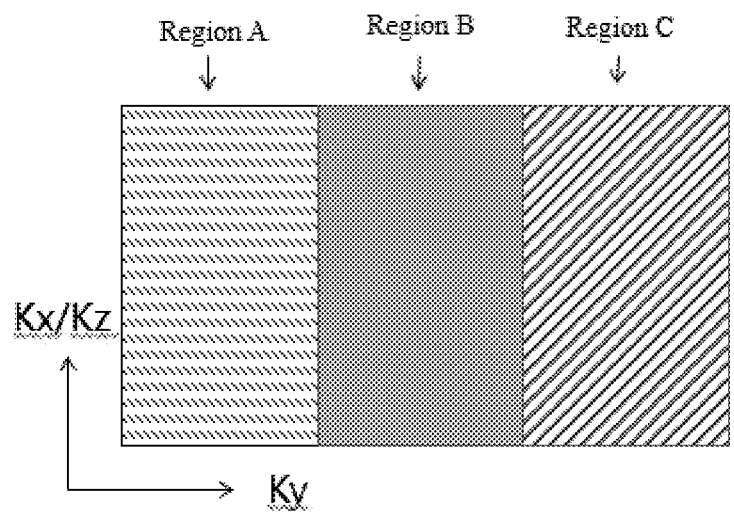
FIG. 10-A
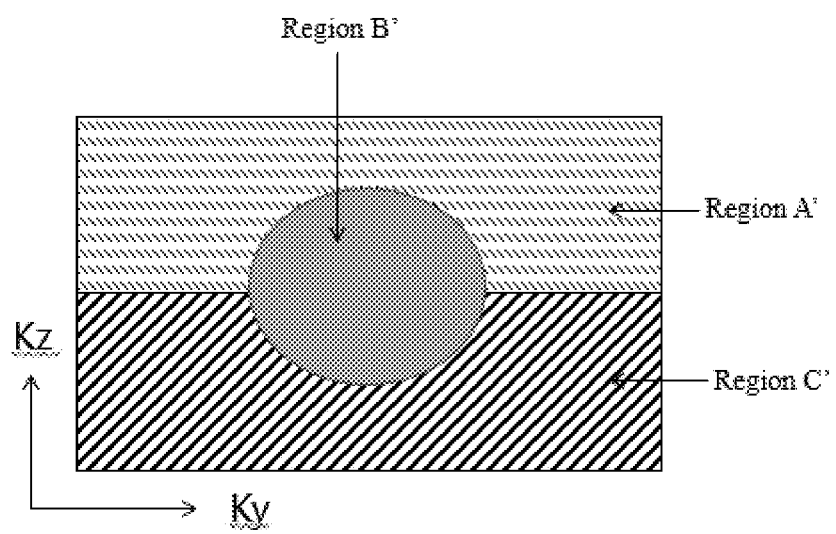
FIG. 10-B

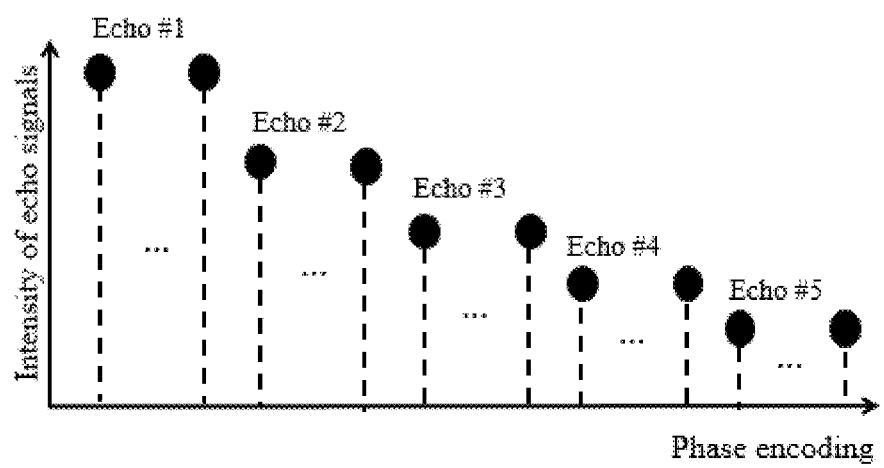
FIG. 13-A
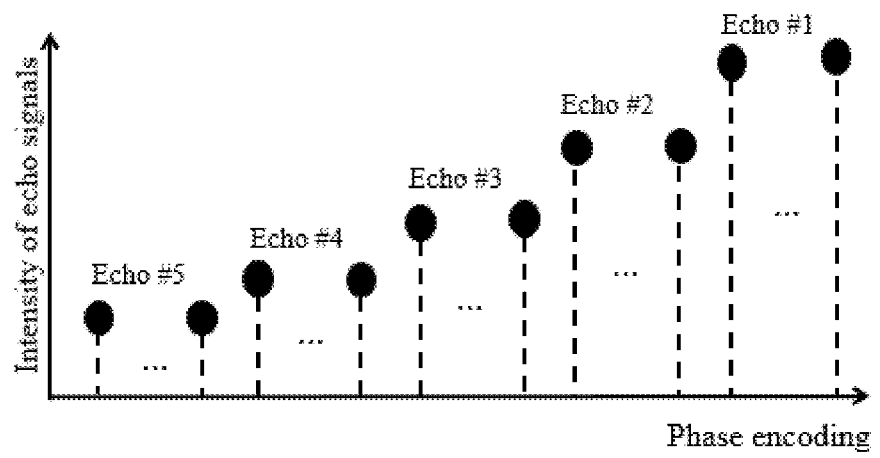
FIG. 13-B

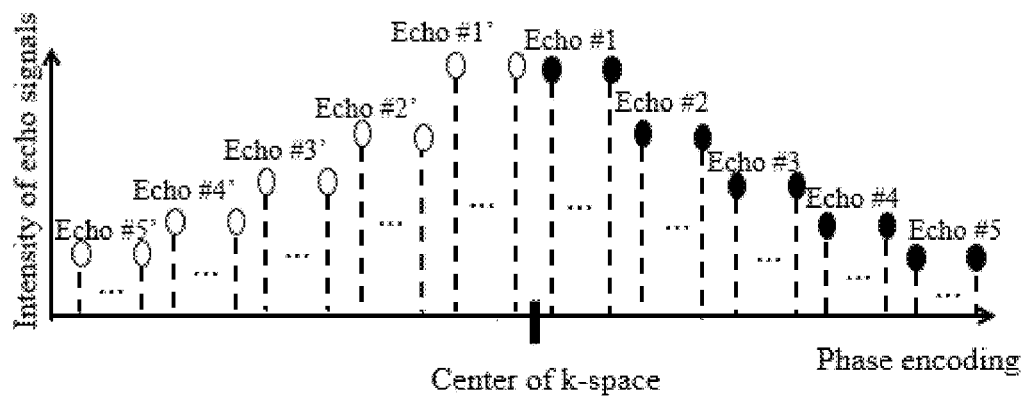
FIG. 14-A
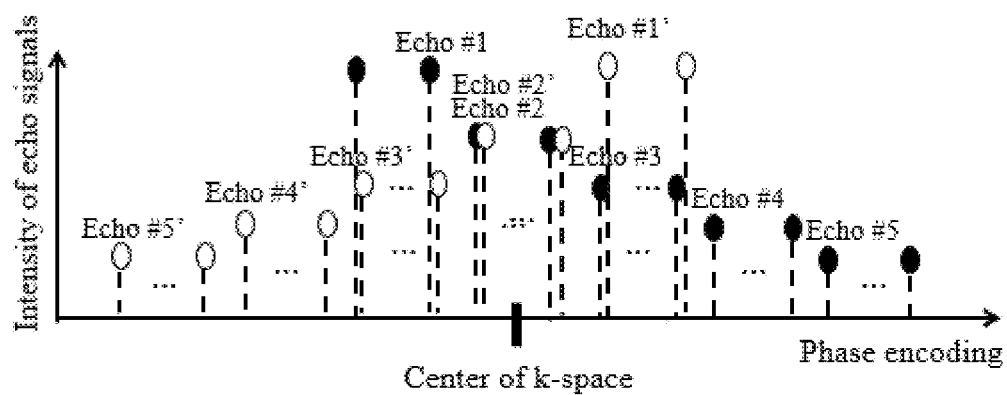
FIG. 14-B

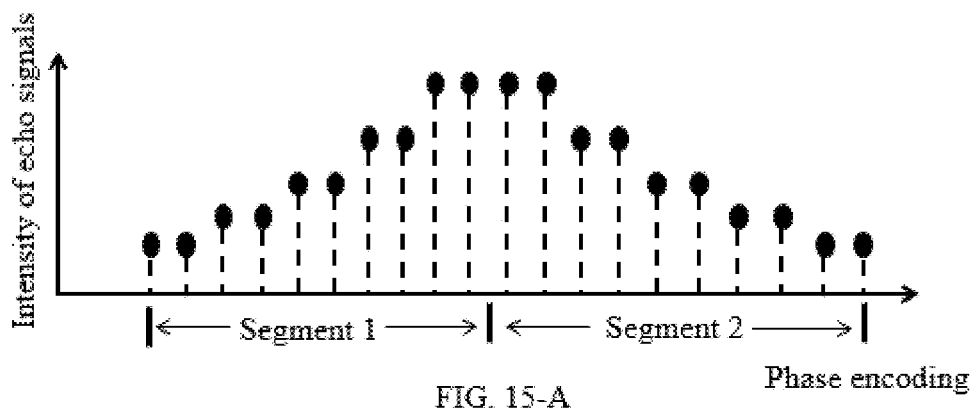
FIG. 15-A
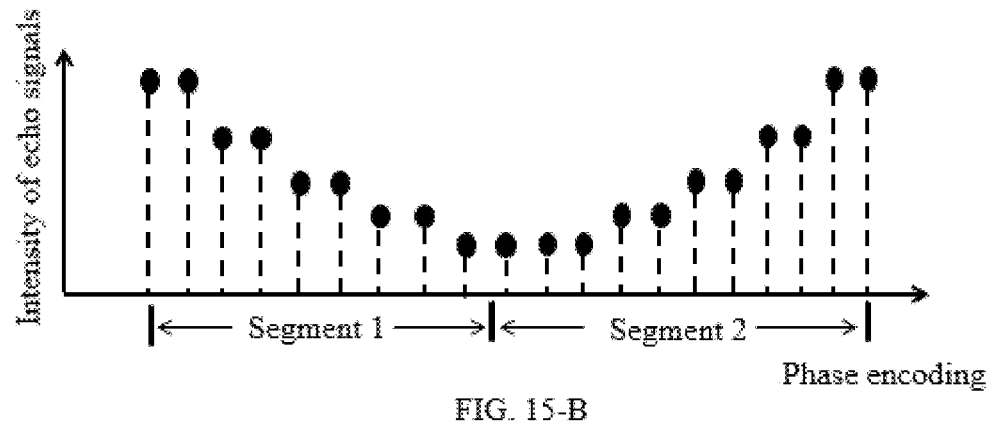
FIG. 15-B

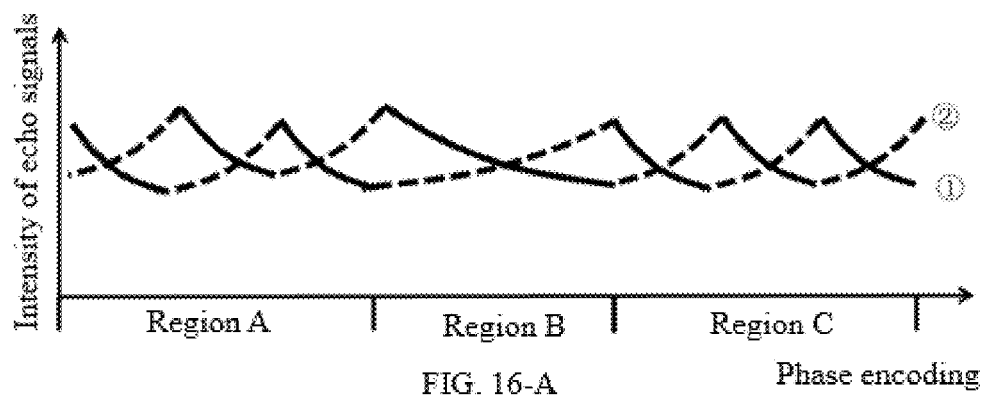
FIG. 16-A
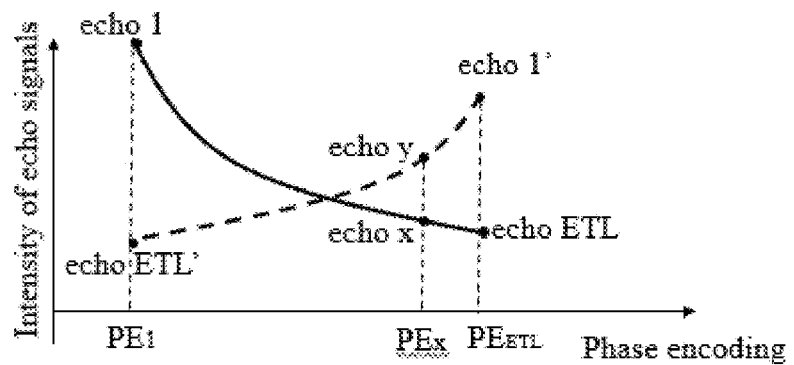
FIG. 16-B

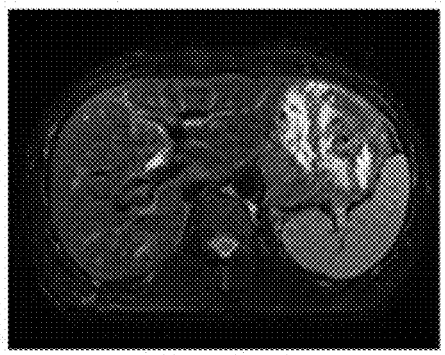
FIG. 17-A
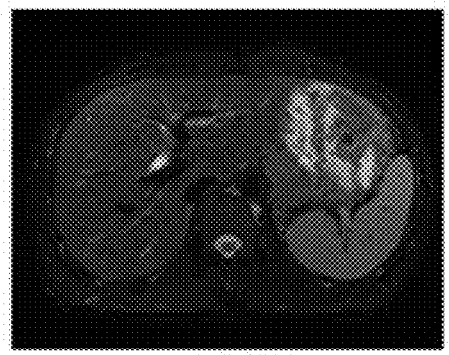
FIG. 17-B
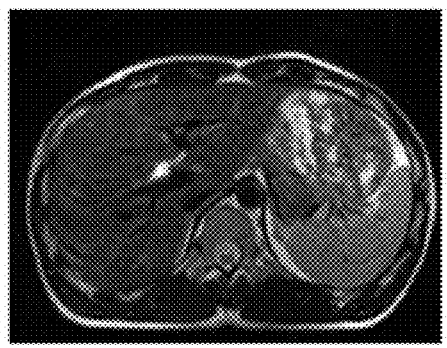
FIG. 17-C
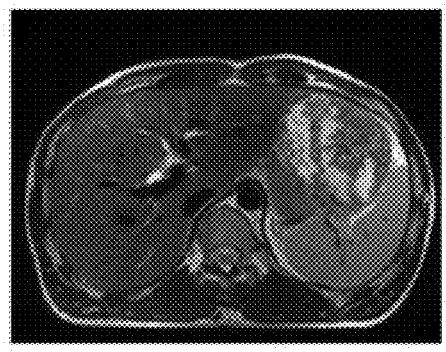
FIG. 17-D

FIG. 18-A
FIG. 18-B

SYSTEM AND METHOD FOR MAGNETIC RESONANCE IMAGING RECONSTRUCTION USING NOVEL K-SPACE SAMPLING SEQUENCES

CROSS-REFERENCE TO RELATED APPLICATIONS

This application is a continuation of U.S. application Ser. No. 15/314,476 filed on Nov. 28, 2016, which is a U.S. national stage under 35 U.S.C. § 371 of International Application No. PCT/CN2016/085412 filed on Jun. 12, 2016, designating the United States of America, which claims priority of Chinese Patent Application No. 201510437221.X filed Jul. 23, 2015, and Chinese. Patent Application No. 201510719200.7 filed Oct. 29, 2015, the entire contents of which are hereby incorporated by reference.

TECHNICAL FIELD

The present disclosure generally relates to magnetic resonance imaging (MRI), and more particularly, to a system and method for data acquisition and data processing in MRI.

BACKGROUND

Magnetic resonance imaging (MRI) is a widely used medical technique which produces images of a region of interest (ROI) by exploiting a powerful magnetic field and radio frequency (RF) techniques. During an MRI process, the acquired signals may be processed and filled into the k-space, then data in the k-space may be transformed to reconstruct MRI images. A fast spin echo (FSE) sequence may be used in an MRI process. During the filling process, the k-space may be divided into several regions. Echoes from different echo trains but in the same position of each echo train may be filled into the same region, and echoes from the same echo train may be filled into different regions. Because of T2 relaxation, a blur may occur in the final reconstructed image. In addition, during a repetition time, if a slight movement of the target occurs, motion artifacts may appear in the reconstructed image. Therefore, it is desirable to suppress the motion artifacts effectively and to make the image clearer.

SUMMARY

In a first aspect of the present disclosure, a method for generating a magnetic resonance (MR) image is provided. The method may include one or more of the following operations. A k-space may be divided into a plurality of regions along a dividing direction. The plurality of regions may include at least a first region including a center of the k-space and a second region different from the first region. An object may be scanned using a plurality of sampling sequences. A plurality of groups of data lines may be acquired. A group of data lines of the plurality of groups may correspond to one of the plurality of sampling sequences, and the group of data lines may be filled into one region of the plurality of regions. A data line may include a plurality of echo signals corresponding to a plurality of echo times respectively. The plurality of groups of data lines may be filled into the plurality of regions of the k-space along one or more filling directions. The filling direction of at least a portion of the first region may be opposite to the filling direction of at least a portion of the second region. An image may be reconstructed based on the plurality of groups of data lines filled into the k-space.

In a second aspect of the present disclosure, a method for generating a magnetic resonance (MR) image is provided. The method may include one or more of the following operations. A k-space may be divided into a plurality of regions along a dividing direction. The plurality of regions may include a first region and a second region. The first region or/and the second region may include at least portion of a center of the k-space. An object may be scanned using a plurality of sampling sequences. A plurality of groups of data lines may be acquired. A group of data lines of the plurality of groups may correspond to one of the plurality of sampling sequences, and the group of data lines may be filled into one region of the plurality of regions. A data line may include a plurality of echo signals corresponding to a plurality of echo times respectively. The plurality of groups of data lines may be filled into the plurality of regions of the k-space along one or more filling directions. The filling direction of at least a portion of the first region may be opposite to the filling direction of at least a portion of the second region. An image may be reconstructed based on the plurality of groups of data lines filled into the k-space.

In a third aspect of the present disclosure, a system for generating a magnetic resonance (MR) image is provided. The system may include a region division block configured to divide k-space into a plurality of regions along a dividing direction, wherein the plurality of regions may include at least a first region including a center of the k-space; an MRI scanner configured to scan an object using a plurality of sampling sequences and to acquire a plurality of groups of data lines, wherein a group of data lines of the plurality of groups may correspond to one of the plurality of sampling sequences, and the group of data lines may be filled into one region of the plurality of regions, and a data line A group of data lines of the plurality of groups may correspond to one of the plurality of sampling sequences, and the group of data lines may be filled into one region of the plurality of regions; a filling block configured to fill the plurality of groups of data lines into the plurality of regions of the k-space along one or more filling directions, wherein the filling direction of at least a portion of the first region may be opposite to the filling direction of at least a portion of the second region; and an image reconstruction block configured to reconstruct an image based on the plurality of groups of data lines filled into the k-space.

In some embodiments, the dividing direction may include a first phase encoding direction, a second phase encoding direction, a linear combination of the first phase encoding direction and the second phase encoding direction, or a radial direction.

In some embodiments, a first direction may be along the dividing direction or opposite to the dividing direction, and a second direction may be opposite to the first direction.

In some embodiments, the plurality of groups of data lines may include a first group of data lines and a second group of data lines. The first group of data lines may be filled into the first region along the first direction, and the second group of data lines may be filled into the first region along the second direction.

In some embodiments, the first group of data lines and the second group of data lines are symmetric with respect to the center of the k-space.

In some embodiments, the first group of data lines and the second group of data lines may include one or more data lines with a same phase encoding. In some embodiments, a weighted averaging process may be performed on the one or more data lines with the same phase encoding.

In some embodiments, the plurality of groups of data lines may include a third group of data lines and a fourth group of data lines. A first portion of the first region may abut a second portion of the second region. The third group of data lines may be filled into the first portion along the first direction, and the fourth group of data lines may be filled into the second portion along the second direction.

In some embodiments, the second region may be divided into a plurality of portions. The plurality of portions may include a third portion and a fourth portion that may abut the third portion. A fifth group of data lines of may be filled into the third portion along the first direction, and a sixth group of data lines may be filled into the fourth portion along the second direction.

In some embodiments, a correction may be performed on at least some groups of the plurality of groups of data lines based on the echo times of the echo signals.

In some embodiments, a fifth portion which is filled with a seventh group of data lines along the first direction in a third region of the plurality of regions may be identified. An eighth group of data lines may be obtained. The eighth group of data lines may be filled into the fifth portion of the third region along the second direction. A weighted averaging process may be performed on the seventh group of data lines and the eighth group of data lines.

In some embodiments, the plurality of groups of data lines may include at least three groups of data lines. Two groups of data lines of the three groups of data lines may include a data line corresponding to zero phase encoding, phase encodings of the other one group of data lines of the three groups of data lines may be larger than or less than the zero phase encoding.

In some embodiments, two groups of data lines using two sampling sequences may be acquired. The filling directions of the two groups of lines may be the same or opposite. The two groups of data lines may include one or more data lines with a same phase encoding.

In some embodiments, the sampling sequence may include a fast spin echo sequence, a half-Fourier acquisition single-shot turbo spin-echo, a turbo gradient spin echo sequence, or an echo planar imaging sequence.

In some embodiments, the second region may not include the center of the k-space.

In some embodiments, the first region and the second region are partially overlapped with each other.

In some embodiments, each group of data lines of the plurality of groups of data lines may include a same number of data lines.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 4-A is a block diagram illustrating an architecture of a processing module according to some embodiments of the present disclosure;

FIG. 4-B is a flowchart illustrating a process for processing MR signals according to some embodiments of the present disclosure;

FIG. 8-A and FIG. 8-B show an exemplary diagram of a k-space filling model as known in the prior art;

FIG. 9-A and FIG. 9-B illustrate an exemplary method for dividing the k-space according to some embodiments of the present disclosure;

FIG. 10-A and FIG. 10-B illustrate an exemplary method for dividing the k-space according to some embodiments of the present disclosure;

FIG. 13-A and FIG. 13-B illustrate filling echoes into the k-space according to some embodiments of the present disclosure;

FIG. 14-A and FIG. 14-B illustrate filling echoes into the region including the center of the k-space according to some embodiments of the present disclosure;

FIG. 15-A and FIG. 15-B illustrate filling echoes into the region not including the center of the k-space according to some embodiments of the present disclosure;

FIG. 16-A and FIG. 16-B illustrate the correction of k-space data according to some embodiments of the present disclosure;

FIG. 17-A through FIG. 17-D illustrate four exemplary images produced from data acquired from the abdomen with different image producing procedures according to some embodiments of the present disclosure; and FIG. 18-A and FIG. 18-B illustrate two exemplary images produced from data acquired from the neck with different image producing procedures according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Figure 1:
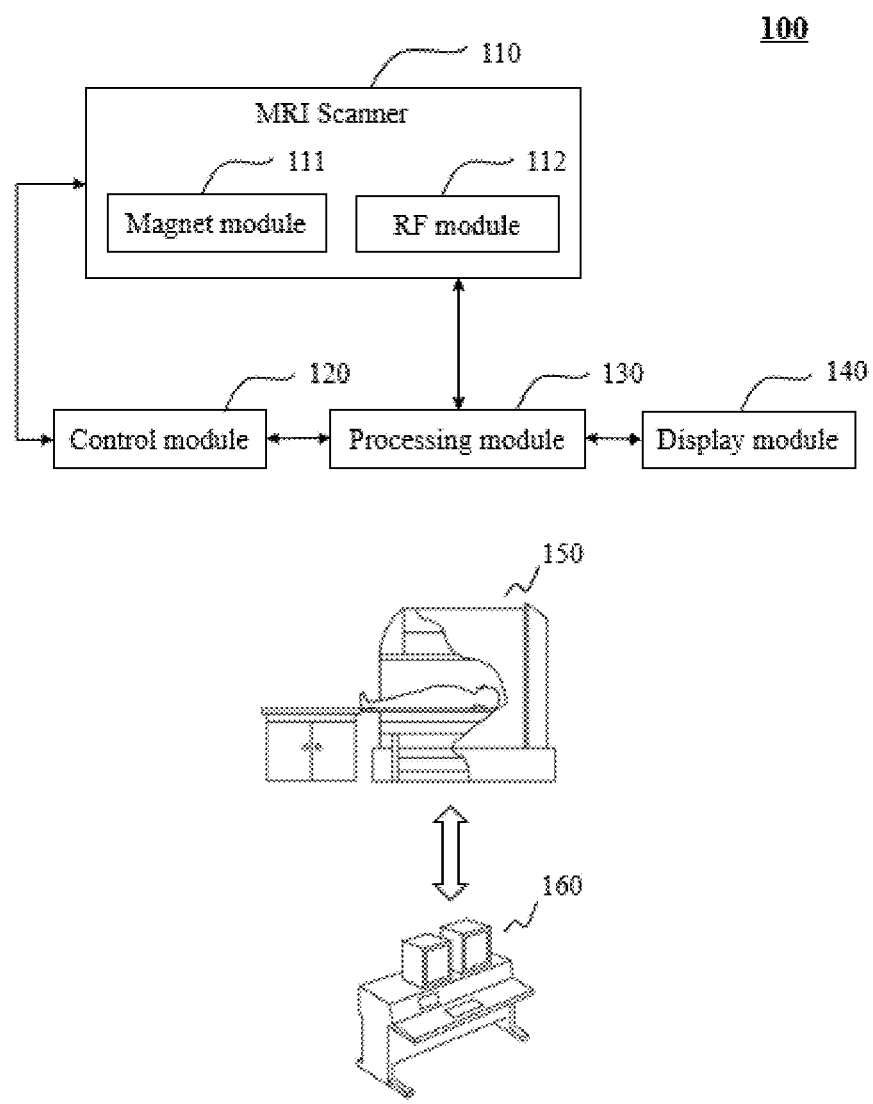
FIG. 1 is a block diagram depicting a magnetic resonance imaging (MRI) system according to some embodiments of the present disclosure.

FIG. 1 is a block diagram of a magnetic resonance imaging system according to some embodiments of the present disclosure. As illustrated, an MRI system 100 may include an MRI scanner 110, a control module 120, a processing module 130, and a display module 140. The MRI scanner 110 may include a magnet module 111 and a radio frequency (RF) module 112. The magnet module 111 may include a main magnet filed generator and/or a gradient magnet field generator (not shown in FIG. 1). The main magnet field generator may create a static magnetic field B0 during an MRI process. The main magnet may be of various types including, for example, a permanent magnet, a super-conducting electromagnet, a resistive electromagnet, etc. The gradient magnet field generator may generate magnet field gradients to the main magnet field B0 in the X, Y, and/or Z directions. The gradient magnet field may encode the spatial information of a subject located in the MRI scanner 110. The RF module 112 may include RF transmitting coils and/or receiving coils. These RF coils may transmit RF signals to or receive RF signals from a subject of interest. In some embodiments, the function, size, type, geometry, position, amount, and/or magnitude of the magnet module 111 and/or of the RF module 112 may be determined or changed according to one or more specific conditions. For example, according to the difference in function and size, the RF coils may be classified as volume coils and local coils. In some embodiments of the present disclosure, the volume coils may include birdcage coils, transverse electromagnetic coils, surface coils, saddle coils, etc. In some embodiments of the present disclosure, the local coils may include birdcage coils, solenoid coils, saddle coils, flexible coils, etc. In some embodiments, the magnet module 111 and the radio frequency (RF) module 112 may be designed to surround a subject to form a tunnel type MRI scanner 150 (i.e. a close-bore MRI scanner), or an open MRI scanner (i.e. an open-bore MRI scanner).

The control module 120 may control the magnet module 111 and/or the RF module 112 of the MRI scanner 110, the processing module 130, and/or the display module 140. The control module 120 may receive information from or send information to the MRI scanner 110, the processing 130, and/or the display module 140. According to some embodiments of the present disclosure, the control module 120 may receive commands from the display module 140 provided by, e.g., a user, and adjust the magnet module 111 and/or RF module 112 to take images of a subject of interest according to the received commands. The processing module 130 may process different kinds of information received from different modules.

For further understanding the present disclosure, several examples are given below, but the examples do not limit the scope of the present disclosure. For example, in some embodiments, the processing module 130 may process MR signals received from the RF module 112 and generate one or more MR images based on these signals and deliver the images to the display module 140. In some embodiments, the processing module 130 may process data input by a user or an operator via the display module 140 and transform the data into specific commands, and supply the commands to the control module 120. The display module 140 may receive input and/or display output information. The input and/or output information may include programs, software, algorithms, data, text, number, images, voice, or the like, or any combination thereof. For example, a user or an operator may input some initial parameters or conditions to initiate a scan. As another example, some information may be imported from an external resource, such as a floppy disk, a hard disk, a wireless terminal, or the like, or any combination thereof. In some embodiments, the control module 120, the processing module 130, and/or the display module 140 may be integrated into an MRI console 160. Users may set parameters in MRI scanning, control the imaging procedure, view the images produced through the MRI console 160.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the assembly and/or function of the MRI system 100 may be varied or changed according to specific implementation scenarios. Merely by way of example, some other components may be added into the MRI system 100, such as a patient positioning module, a gradient amplifier module, and other devices or modules. Note that the MRI system may be a traditional or a single-modality medical system, or a multi-modality system including, e.g., a positron emission tomography-magnetic resonance imaging (PET-MRI) system, a remote medical MRI system, and others, etc. However, those variations and modifications do not depart from the scope of the present disclosure.

Figure 2:
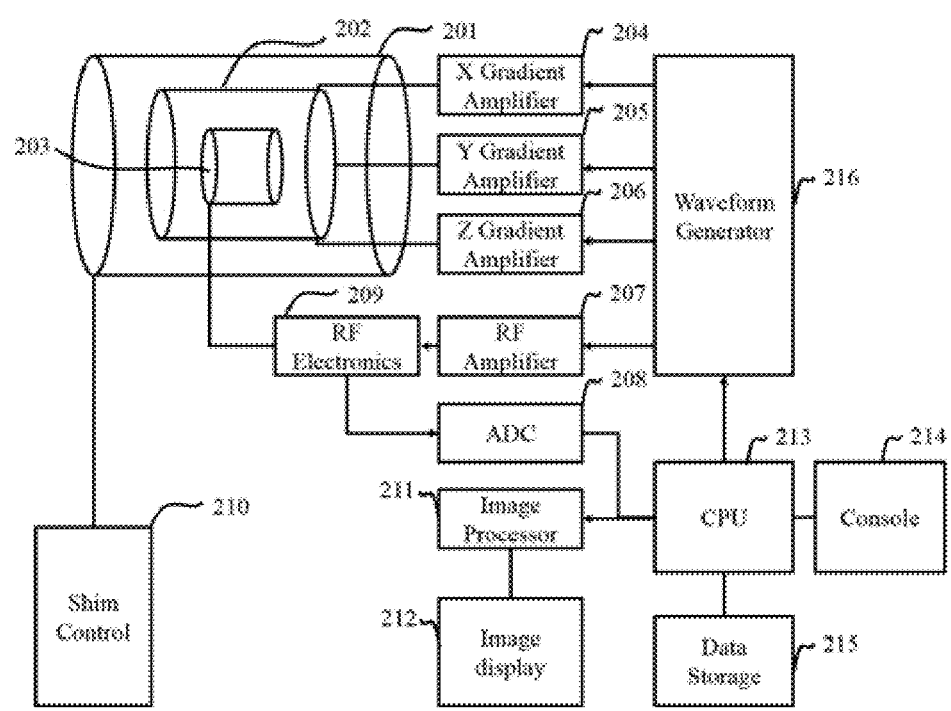
FIG. 2 is a block diagram depicting an MRI system according to some embodiments of the present disclosure.

FIG. 2 is a block diagram of the MRI system 100 according to some embodiments of the present disclosure. As shown in the figure, the main field and shim coils 201 may generate a main magnetic field that may be applied to an object (also referred to as subject) exposed inside the field. The main filed and shim coils 201 may also control the homogeneity of the generated main field. Gradient coils 202 may be located inside the main field and shim coils 201. The gradient coils 202 may generate a second magnetic field or referred to as a gradient field. The gradient coils 202 may distort the main field generated by the main field and shim coils 201 so that the magnetic orientations of the protons of an object may vary as a function of their positions inside the gradient field. The gradient coils 202 may include X coils, Y coils, and/or Z coils (not shown in the figure). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of MR signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 204, and/or the Z gradient amplifier 204. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction.

RF coils 203 may generate a third magnetic field that is utilized to generate MR signals for image construction. In some instances, the RF coils 203 may include a transmitting coil and a receiving coil. In some embodiments, the RF coils 203 may be in connection with RF electronics 209 that may be configured or used as one or more integrated circuits (ICs) functioning as a waveform transmitter and/or a waveform receiver. The RF electronics 209 may be connected with an RF amplifier 207 and an analog-to-digital converter (ADC) 208. The waveform generator 216 may generate an RF signal. The RF signal may be first amplified by the RF amplifier 207, processed by the RF electronics 209, and applied on the RF coils 203 to generate a third magnetic field, in addition to the magnetic fields generated by, e.g., the main filed and shim coils 201 and the gradient coils 202. In some embodiments of the present disclosure, the waveform generator 201 may generate a series of RF waveforms periodically or aperiodically. For instance, the waveform generator 216 may generate an excitation RF pulse with a flip angle of 90° and multiple refocusing RF pulses with a flip angle of 180°. Note that the excitation RF pulse may have a flip angle other than 90°, e.g., any magnitude ranging from 0° to 180°. An excitation RF pulse with a flip angle of 90° is mentioned elsewhere in the present disclosure for illustration purposes, and is not intended to limit the scope of the present disclosure. An excitation RF pulse with a flip angle other than 90° may be used.

As described elsewhere in the present disclosure, the flip angle of a refocusing RF pulse may be of a value other than 180°. Furthermore, the waveform generator 216 may generate a series of RF waveforms periodically or aperiodically. For instance, the waveform generator 216 may generate an excitation RF pulse with a flip angle of 90° and multiple refocusing RF pulses with same flip angles or variable flip angles. The flip angle of the excitation RF pulse may be variable as well. The excitation RF pulse may be utilized to generate the third magnetic field, and with the application of one or more refocusing RF pulses, one or more MR signals may be generated. For instance, an echo train with multiple echoes may be generated. The echo train length (ETL) may be either fixed or variable. For instance, for a same tissue to be imaged, ETL may be fixed. For different tissues, ETL may be variable. Furthermore, even for a same tissue, ETL may be variable. The echo train may be received by the receiving coils of the RF coils 203. Then the echo train may be sent to the RF electronics 209, and transmitted to the ADC 208 for digitization. The echo train may be demodulated and filtered in the electronics 209. Subsequently, the echo train may be processed by an image processor 211, e.g., with the assistance of the CPU 213, to generate one or more images. A console 214 may communicate through a link with the CPU 213 and allow one or more operators to control the production and/or display of images on image display 212. The console 214 may include an input device, a control panel (not shown in the figure), etc. The input device may be a keyboard, a touch screen, a mouse, a remote controller, or the like, or any combination thereof.

The CPU 213 may control the production of the waveforms in the waveform generator 216, and the production of images in the image processor 211. The CPU 213 may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof.

The data storage 215 may store received MR signals. When an MRI scan is completed and the whole data of a scanned object (e.g., a tissue or a specific part of a body) is acquired. A Fourier transform of the data may be performed by, without limitation to, the CPU 213, the image processor 211, or the like, or any combination thereof. After the transform is completed, one or more desired images may be generated. The images may be stored in the data storage 215. The images may be further conveyed to the image display 212 for display. A shim control 210 may be utilized to control the homogeneity of the main magnetic field generated by the main field and shim coils 201.

It should be noted that the above description of the MRI system is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure.

Figure 3:
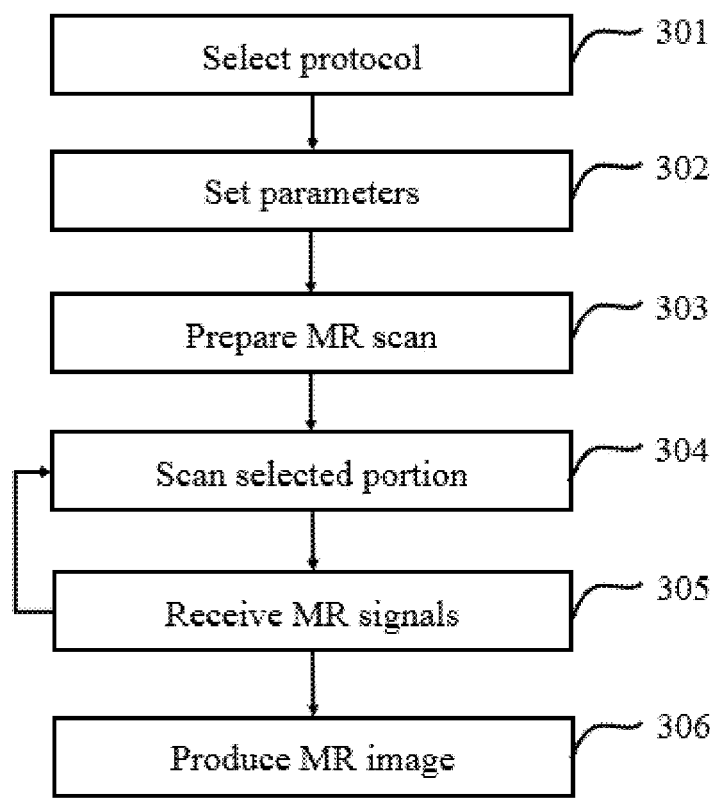
FIG. 3 is a flowchart illustrating a process for MRI according to some embodiments of the present disclosure.

FIG. 3 depicts a flowchart of an MR scan that may be performed according to some embodiments of the present disclosure. In step 301, one or more protocols may be selected. A protocol may be designed for one or more tissues to be imaged, diseases, and/or clinical scenarios. A protocol may contain a certain number of pulse sequences oriented in different planes and/or with different parameters. The pulse sequences may include a spin echo sequence, a gradient echo sequence, a diffusion sequence, an inversion recovery sequence, or the like, or any combination thereof. For instance, the spin echo sequences may include fast spin echo (FSE), half-Fourier acquisition single-shot turbo spin-echo (HASTE), turbo gradient spin echo (TGSE), or the like, or any combination thereof. When an MR scan is to be conducted, an operator may select a protocol for the scan. For example, for a cranial scan, the operator may select any one of the protocols called "Routine Adult Brain," "MR Angiogram Circle of Willis," and many others. These protocols described above or other protocols may be stored in the data storage 215 as illustrated in FIG. 2, or other storage devices (e.g., an external storage device or server accessible by the MR system 100).

Parameters may be set in step 302. The parameters may be set via the console 214 through a user interface that may be displayed on, e.g., the image display 212 as specified in FIG. 2. The parameters may include image contrast and/or ratio, a region of interest (ROI), slice thickness, an imaging type (e.g., T1 weighted imaging, T2 weighted imaging, proton density weighted imaging, etc.), T1, T2, a spin echo type (spin echo, fast spin echo (FSE), fast recovery FSE, single shot FSE, gradient recalled echo, fast imaging with steady-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

According to some embodiments of the present disclosure, the term "phase" may refer to a segment, section, part or fragment of a series of flip angles (or a flip angle schedule) corresponding to an echo train divided according to some principles. The number of phase(s) and/or the number of echo(es) in each phase may depend on specific conditions. In some embodiments, an echo train may be divided into several phases according to considerations including, e.g., the characteristics of a reference signal schedule, a desired signal evolution, etc. Merely by way of example, the reference signal schedule of an echo train may be divided into three segments, regardless of what their values are or how their trends vary (e.g. firstly exponential decay, secondly essentially flat, and lastly exponential decay again), then the echo train may be divided into three phases accordingly. In some embodiments, the reference signal schedule may be divided into different phases according to one or more other considerations. For example, only one or several specific echo(es) associated with resultant signal(s) of interest need to be paid attention to. For example, it is desired that the signals corresponding to two echoes meet one or more thresholds; the echo train may belong to a single phase so that the two echoes of interest are located in the same phase; the echo train may be divided into two or more phases, and the two echoes of interest may be located in a same phase or different phases. In some embodiments, there may be no reference signal schedule at all, and the number of phase(s) and/or the number of echo(es) in each phase may be determined based on, e.g., a random division, an equal division, a certain rule, or the like, or any combination thereof. The certain rule may include Arithmetic progression, Geometric progression, Cauchy sequence, Farey sequence, look-and-say sequence, or the like, or a variation thereof, or any combination thereof.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the number of phases in an echo train may be one, two, three, or more, or equal to the number of echoes. In some embodiments, several echoes may be located in one phase, and the remaining echoes belong to one or more other phases or are not assigned to a phase at all. However, those variations and modifications do not depart from the scope of the present disclosure.

Preparation for the MR scan may be performed in step 303. The preparation may include placing an object, e.g., a selected portion of a subject of interest, within the scanning area, setting the scanning range, tuning and matching shimming coils, adjusting a center frequency, adjusting transmitter attenuation/gain, adjusting signal reception attenuation/gain, setting dummy cycles, or the like, or any combination thereof.

The selected portion of a subject of interest may be scanned in step 304. The scanning may include localizer scans, calibration scans for parallel imaging, automatic pre-scan, or the like, or any combination thereof. For instance, the localizer scans may produce localizer images of low resolution and a large field of view (FOV). Such localizer images may be utilized in subsequent steps. In this step, a pulse sequence including, for example, an excitation RF pulse and a series of refocusing RF pulses, may be applied on the selected portion. The flip angles of the refocusing RF pulses may be either fixed or variable.

MRI is a non-invasive imaging technique that uses a powerful main magnet field to align the nucleus spins in a subject (or a portion thereof). When the subject is exposed in a magnetic field (main magnet field B0), the nucleus spins of the subject tend to align with field B0, but may still precess at the Larmor frequency. The overall motion of the nucleus spins in the subject, subject to field B0, may be simplified as net magnetization (M) that is the averaged sum of many individual nucleus spins. The net magnetization M may be broken down into a longitudinal component (along the Z axis, aligned with field B0), and a transverse component (within the XY plane). With the effect of main magnet field B0, M may constitute a longitudinal magnetization vector in the macroscopic angle. A second magnetic field, RF field (field B1), may be applied to M, oscillating the Larmor frequency, and causing M to precess away from the field B0 direction. During the excitation by radio frequency, longitudinal magnetization may decrease and transverse magnetization may appear. Merely by way of example, if an excitation RF pulse with a 90° flip angle is applied, when the RF transmitter is turned off, there is no longitudinal magnetization any more, and only transverse magnetization exists. The transverse magnetization may induce a current signal in the RF receiving coils, and the induced current may be referred to as an MR signal. The MR signal may correspond to one or more echo trains including, for example, one or more echo signals, according to the pulse sequence selected in step 301.

Generated MR signals may be received in step 305. Step 305 may be performed by the RF coils 203 as described in FIG. 2. The MR signals may correspond to one or more echo trains, or the like. It should be noted that step 305 and step 304 may be repeated until sufficient data to generate an image is acquired or an image is generated. One or more operations may be performed on the MR signals to produce images of the selected portion. The operations may further include Fourier transform (FT) of the data in k-space, frequency encoding, phase encoding, or the like, or any combination thereof. The operations may include filling data of the MR signals into the Fourier domain (or referred to as the spatial frequency space, or the k-space). For instance, Fourier transform may be a fast Fourier Transform (FFT), a 2-dimentional FT, a 3-dimentional FT, or the like, or any combination thereof. In step 306, one or more images of the selected portion may be produced. The images may be displayed on, e.g., the image display 212 (shown in FIG. 2), or other display devices (e.g., an external display device).

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For instance, step 301, step 302, and step 303 may be performed sequentially at an order other than that described above in connection with FIG. 3. Alternatively, step 301, step 302, and step 303 may be performed concurrently.

FIG. 4-A is a block diagram illustrating the processing module 130 according to some embodiments of the present disclosure. The processing module 130 as illustrated in FIG. 1 may process information before, during, or after an imaging procedure. Note that the construction of the processing module 130 may have some other variations, and that FIG. 4A is provided for illustration purposes. The processing module 130 may include a CPU. The CPU may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof. As shown in FIG. 4-A, the processing module 130 may include a computing unit 401, an image producing unit 402, a storage unit 403, and an A/D converter.

The computing unit 401 may calculate different kinds of information generated from the MRI scanner 110, or received from the control module 120 and/or display module 140. The information from the MRI scanner 110 may be a plurality of MR signals of a subject. The information from the control module 120 may include information about the MRI scanner 110, the magnet module 111, a patient position (e.g., within an MRI system), the RF module 112, or the like, or any combination thereof. In some embodiments, the information may be a patient position, the main and/or gradient magnet intensity, the radio frequency phase and/or amplitude, and so on. The information from the display module 140 may include information from a user and/or other external resource. Exemplary information from a user may include parameters regarding image contrast and/or ratio, a subject of interest (e.g., the type of tissue to be imaged, etc.), slice thickness, an imaging type (e.g., T1 weighted imaging, T2 weighted imaging, proton density weighted imaging, etc.), T1, T2, a spin echo type (e.g., spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

The image producing unit 402 may process the data such as magnetic resonance (MR) signals acquired from the subject of interest and reconstruct them into an MR image. The image producing unit 402 may spatially decode an MR signal that has been spatially encoded by the magnetic field(s). The intensity or magnitude of the signal, and other properties such as a phase number, a relaxation time (T1 or T2), magnetization transfer, or the like, may be ascertained. The image producing unit 402 may employ different kinds of imaging reconstruction techniques for the image reconstruction procedure. Exemplary image reconstruction techniques may include Fourier reconstruction, constrained image reconstruction, regularized image reconstruction in parallel MRI, or the like, or a variation thereof, or any combination thereof.

The storage unit 403 may store the information that may be used by the computing unit 401 and/or the image producing unit 402. The information may include programs, software, algorithms, data, text, number, images and some other information. These examples are provided here for illustration purposes, and not intended to limit the scope of the present disclosure. Algorithms stored in the storage unit 403 may include recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof. In some embodiments, the storage unit 403 may store MR signals. In some embodiments, the storage unit 403 may share the same storage with the data storage 215 in FIG. 2.

The A/D converter 404 may convert analog MR signals to digital MR signals. In some embodiments, one or more parameters may be set before or during the conversion, e.g., voltage, current, rate, sampling frequency, or the like, or a combination thereof. The converted MR signals may be stored in the storage unit 403 or the data storage 215.

It should be noted that the above description of the processing module 130 is merely provided for the purposes of illustration, and not intended to limit the scope of the present disclosure. For persons having ordinary skills in the art, multiple variations or modifications may be made under the teachings of the present disclosure. For example, the assembly and/or function of processing unit may be varied or changed. In some embodiments, the computing unit 401 and the image producing unit 402 may share one storage unit 403. While in some embodiments, the computing unit 401 and the image producing unit 402 may have their own storage blocks, respectively. However, those variations and modifications do not depart from the scope of the present disclosure.

FIG. 4-B is a flowchart illustrating a process for processing MR signals according to some embodiments of the present disclosure. In step 411, echo signals may be acquired. The echo signals may be acquired by the MRI scanner 110, or may be read from the data storage 215, or an external resource including, for example, a floppy disk, a hard disk, a wired terminal, a wireless terminal, or the like, or any combination thereof. The echo signals acquired may be phase encoded, and/or frequency encoded. The echo signals may be acquired from a plurality of shots of a RF pulse sequence. In some embodiments, the echo signals may be acquired in different orders, for example, the echo signals of relatively lower phases may be acquired first, and that of higher phases may be acquired subsequently. The acquired echo signals may be analog or digital. In some embodiments, the analog echo signals acquired may be converted from analog signals to digital signals in step 412. The analog-to-digital conversion may be performed by the A/D converter 404. The digitized echo signals may include a plurality of data points, wherein each data point may have a specific spatial frequency (i.e., a specific phase and a specific frequency). Further, each data point digitized from the echo signals may be a complex number with real and imaginary components. Alternately, each data point may be defined as having one or more factors, e.g., amplitude, phase, or the like. In some embodiments, the amplitude and phase of a data point may be computed by a trigonometric relation. The digitized echo signals may be further stored in step 413. The digitized echo signals may be stored in the data storage 215 of the MRI system, the storage unit 403 of the processing module 130, or an external storage medium including, for example, a floppy disk, a hard disk, a wired terminal, a wireless terminal, or the like, or any combination thereof.

Then the echo signals may be computed in step 414. Computation of the echo signals may include a Fourier transform, an interconversion of the data in Cartesian coordinate system and data in polar coordinate system (i.e., an interconversion of data with real and imaginary components and data with amplitude and phase components). In some embodiments, computation may be performed to correct the echo signals. Computation of the echo signals may include weighted calculation, averaging, optimization, data filtering, data screening, or the like, or a combination thereof. The computation process may be performed by the computing unit 401.

Afterwards, the echo signals may be used to produce an MR image in step 415. Generally, the echo signals may be filled into the k-space, processed by one or more algorithms, and an image may be reconstructed.

The image may be produced by the image producing unit 402. In some embodiments, during the imaging producing, the process may return to step 414 for obtaining data until a complete image is produced.

It should be noted that the above description of the flowchart in FIG. 4-B is merely provided for the purposes of illustration, and not intended to limit the scope of the present disclosure. For persons having ordinary skills in the art, multiple variations or modifications may be made under the teachings of the present disclosure. For example, the storage of the echo signals in step 413 may be not necessary. Alternatively, an image storage step may be added after step 415. As another example, the computation step 414 may be combined with the image producing step 415. However, those variations and modifications do not depart from the scope of the present disclosure.

Figure 5:
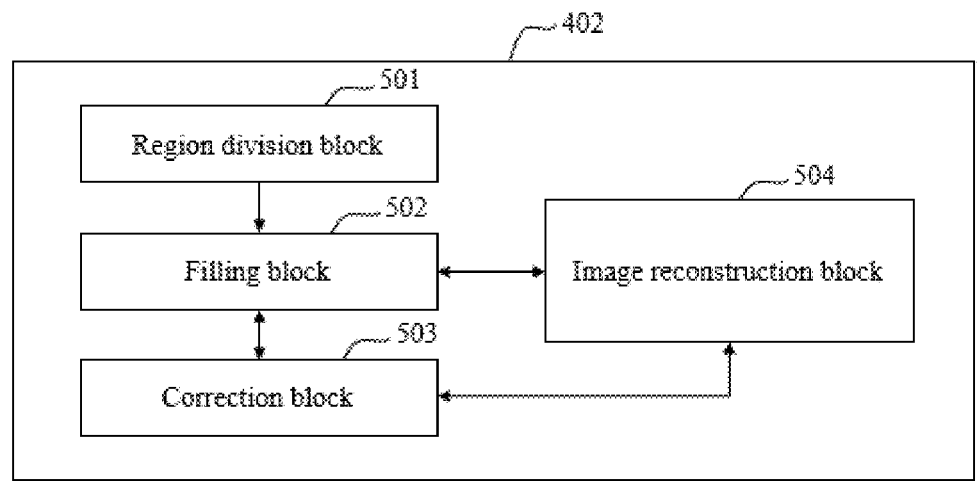
FIG. 5 is a block diagram illustrating an architecture of an image producing unit according to some embodiments of the present disclosure.

FIG. 5 is a block diagram illustrating an architecture of the image producing unit 402 according to some embodiments of the present disclosure. The image producing unit 402 may include a region division block 501, a filling block 502, a correction block 503, and an image reconstruction block 504. The region division block 501 may divide the k-space into a plurality of regions. In some embodiments, the number of the regions may be fixed or variable. The number of the regions may be set by the default of the system, or may be adjusted for the scanning of different ROIs of a subject, or the same or different ROIs of different subjects. In some embodiments, the size of any region in the k-space may be fixed or variable. In some embodiments, the sizes of the plurality of regions may be the same as or different from each other. In some embodiments, the plurality of the regions may be divided along a dividing direction. The dividing direction may be the phase encoding direction ky or kz, or any linear combination direction of ky and kz (e.g., the radial orientation kr). For example, when the plurality of the regions may be divided along the phase encoding direction, the phase encoding of the k-space may include a plurality of phase encoding lines illustrated as a set {PE1, PE2, . . . , PEi, . . . , PEN, PE1<PE2< . . . <PEi< . . . <PEN, i<N}, and a plurality of regions with the phase encoding ranges of PE1-PEi, PEi+1-PEi+x, . . . , PENj~PEN may be obtained after division. As used herein, PE refers to "phase encoding." Any one of N, x, and j may be a real integral number.

In some embodiments, for two adjacent regions among the plurality of regions, their phase encoding ranges may partially overlap. As used herein, the phrase "two adjacent regions" may represent that one region abuts the other region. In some embodiments, for two adjacent regions among the plurality of regions, their phase encoding ranges do not overlap. Merely by way of example, the phase encoding ranges of two adjacent regions a and b are PEi+1~PEi+x and PEj+1~PEj+y (j>i, and y is a real integer), respectively;

the phase encoding lines of the edges of the two regions may satisfy a relationship described by: j+1≤i+x (indicating that the two adjacent regions partially overlap), or j+1=i+x+1 (indicating that the two adjacent regions do not overlap). In some embodiments, one of the plurality of regions may include the center of the k-space, which may be illustrated as PE0−i~PE0+j, where i≥1, j≥1 and i may be to the same as or different from j. In some embodiments, the region including the center of the k-space may be illustrated as PE0−i~PE0 or PE0~PE0+j, wherein i≥1, and i may be to the same as or different from j.

The filling block 502 may fill echo signals into the plurality of regions of the k-space. An echo signal may correspond to a phase encoding line, and the echo signal or data of the echo signal may be filled into a corresponding phase encoding line of a region of the k-space. In some embodiments, the regions of the k-space may be filled in an order according to a system setting. In some embodiments, the regions of the k-space may be filled in an order that is different from a system setting. In some embodiments, the filling order may be consistent with the phase encoding order, or may be adjusted based on the priority levels of the regions, or the like, or any combination thereof. For example, the filling order may be consistent with the phase encoding order, either from the minimum encoding to the maximum encoding, or from the maximum encoding to the minimum encoding, or randomly. As used herein, suppose that the range of the k-space along the phase encoding direction may be [−127, +128], the minimum encoding may refer to the phase encoding line of ky=−127, and the maximum encoding may refer to the phase encoding line of ky=+128. As another example, the regions that have a relatively lower phase encoding or locate close to the center of the k-space may be filled preferentially. As used herein, "preferentially" may indicate that the regions may be filled first, and the other regions may be filled subsequently.

In some embodiments, the order of filling the echo signals or data into the regions of the k-space may be based on the order the echo signals are acquired. For example, three echo signals (echo 1, echo 2, and echo 3) of an echo train are acquired sequentially; the filling order may be in accordance with the acquisition order (echo 1, echo 2, echo 3), or opposite to the acquisition order (echo 3, echo 2, echo 1). As used herein, the echo train may refer to an echo line including a plurality of echoes generated within a single repetition time. As used herein, the repetition time may refer to the time between the applications of two consecutive excitation RF pulses.

In some embodiments, the filling may take place at the time the echo signals are acquired. In some embodiments, the echo signals may be stored and subsequently retrieved to be filled into the k-space. In some embodiments, the echo signals of the same echo train may be used to fill into the same region of the k-space. For instance, there is a region with a phase encoding range of PEi+1~PEi+x (x≥5); three echo signals in a same echo train (echo 1, echo 2, and echo 3) of which the phase encodings are PEi+1, PEi+3, and PEi+5, respectively; the three echo signals may be filled into the specific sites (or "phase encoding line") PEi+1, PEi+3, and PEi+5 of the region PEi+1~PEi+x.

The correction block 503 may correct the echo signals or data filled into the k-space. For an echo train, the intensity of the echo signals may attenuate with the passage of the acquisition time, and the intensity attenuation of the echo signals may cause errors and reduce the image quality. A correction may be performed. For instance, at an adjoining (but not overlapping) region of two adjacent regions, an abrupt intensity change may occur (see, for example, FIG. 12). A correction may be performed to avoid or alleviate the abrupt intensity change. For instance, a weighted averaging process may be performed on the data to be filled into the adjoining region (see, for example, FIG. 16-A and FIG. 16-B). As another example, two adjacent regions PEi+1~PEi+x (region 1) and PEj+1~PEj+y (region 2) (j>i, and j+1≤i+x) partially overlap, forming an overlapping region (see, e.g., FIG. 9-A and FIG. 9-B). The data (or "echo signals") filled into the adjacent regions may be from different echo trains generated by the FSE sequence. The overlapping region may be filled with data from different echo trains generated by the FSE sequence (see, e.g., FIG. 11). To reduce or eliminate the data overlapping in the overlapping region, a correction may be performed, e.g., a weighting process may be performed.

The image reconstruction block 504 may reconstruct an image according to the k-space data. Different kinds of techniques may be used for image reconstruction. In some embodiments, the image reconstruction techniques may include but not limited to Fourier reconstruction, inverse Fourier transform, constrained image reconstruction, regularized image reconstruction in parallel MRI, or the like, or any combination thereof.

It should be noted that the above description of the block diagram in FIG. 5 is merely provided for the purposes of illustration, and not intended to limit the scope of the present disclosure. For persons having ordinary skills in the art, multiple variations or modifications may be made under the teachings of the present disclosure. For example, the region division block 501 may be not necessary and may be integrated in the filling block 502. As another example, any two of the blocks may be integrated into a single block. However, those variations and modifications do not depart from the scope of the present disclosure.

Figure 6:
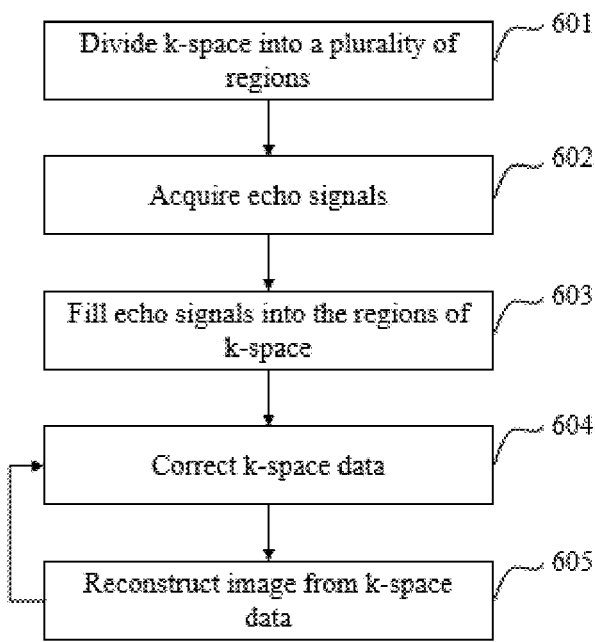
FIG. 6 is a flowchart illustrating a process for producing images according to some embodiments of the present disclosure.

FIG. 6 is a flowchart illustrating a process for producing images according to some embodiments of the present disclosure. In step 601, the k-space may be divided into a plurality of regions. The region division may be performed by the region division block 501. The plurality of regions may be divided along a dividing direction. The dividing direction may be the phase encoding direction ky or kz, or any linear combination direction of ky and kz (e.g., the radial orientation kr). In some embodiments, the size or shape of the region may be fixed or variable. For example, if in a Cartesian coordinate system, the shape may be rectangle, square, rhombic, or the like. As another example, if in a polar coordinate system, the shape may be circular, elliptic, sectorial, ring, or the like. In some embodiments, the plurality of regions may be continuous along the dividing direction, or one or more overlapping regions may occur between any two adjacent regions. The size or shape of the overlapping region may be fixed or variable, and the sizes or shapes of the one or more overlapping regions may be the same or different with each other.

In step 602, echo signals may be acquired. The echo signals may be acquired by the MRI scanner 110, or may be read from the data storage 215, the storage unit 403, or an external resource including, for example, a floppy disk, a hard disk, a wired terminal, a wireless terminal, or the like, or any combination thereof. The echo signals acquired may be phase encoded, and/or frequency encoded. The echo signals may be acquired from one or more FSE sequences. In some embodiments, the acquired echo signals may be converted from analog signals to digital signals.

In step 603, the acquired echo signals may be filled into the plurality of regions of the k-space. The filling process may be performed by the filling block 502. The echo signals may be filled into the regions along a filling direction. The filling direction may be the phase encoding direction, or opposite to the phase encoding direction. The echo signals may be filled into the regions according to a filling order. The filling order may be according to a default setting of the system, or may be set by a user (e.g., an operator). In some embodiments, one or more regions of the k-space may be filled with echo signals generated by one or more FSE sequences. For a specific region, an echo train including a plurality of echoes (also referred to as echo signals) including echo 1, echo 2, echo 3, . . . , echo N; the echo signals may be filled into the region sequentially (e.g., from echo 1 to echo N), or in another filling order (e.g., from echo N to echo 1). For multiple regions, the filled echo signals may be generated by a plurality of FSE sequences. In some embodiments, the region(s) of which the phase encoding is relatively low or is close to the center of the k-space may be filled preferentially. As used herein, "preferentially" may indicate that the regions may be filled first, and the other regions may be filled subsequently.

The data (or "echo signal(s)") filled in the k-space may be corrected in step 604. The correction process may be performed by the correction block 503. In some embodiments, the correction may be performed in connection with the data in an overlapping region. For instance, a weighting process may be performed in an overlapping region. In some embodiments, the intensity of the echo signals may attenuate with the passage of the acquisition time along the echo train, and the correction may be performed to reduce or eliminate the effect of the signal attenuation. For example, two or more sets of echo signals may be filled into two adjacent regions along opposite filling directions (see, e.g., FIG. 16-A and FIG. 16-B).

Then an image may be reconstructed in step 605 based on the corrected data in the k-space in step 604. The image reconstruction process may be performed by the image reconstruction block 504. The image reconstruction techniques may include Fourier reconstruction, constrained image reconstruction, regularized image reconstruction in parallel MRI, or the like, or any combination thereof. In some embodiments, if the reconstructed image is not qualified (e.g., the noise exceeds a threshold, or conspicuous artifacts exist), the procedure may return to step 604 for further correction, and the step 605 and step 604 may be repeated until an qualified image may be constructed.

It should be noted that the above description of the flowchart in FIG. 6 is merely provided for the purposes of illustration, and not intended to limit the scope of the present disclosure. For persons having ordinary skills in the art, multiple variations or modifications may be made under the teachings of the present disclosure. For example, the region division step 601 may be not necessary, as the region division manner may be pre-stored in the system. As another example, a process of FSE excitation may be added in the acquisition step 602 to generate corresponding echo trains. As another example, data processing may be added in the correction step 604 to eliminate image artifacts including Gibbs artifact, motion artifact, flow artifact, metal artifact, chemical shift artifact, partial volume artifact, wrap around artifact, or the like, or any combination thereof. As another example, a criterion may be set in the correction step 604 or the reconstruction step 605 for image quality judgement. However, those variations and modifications do not depart from the scope of the present disclosure.

Figure 7:
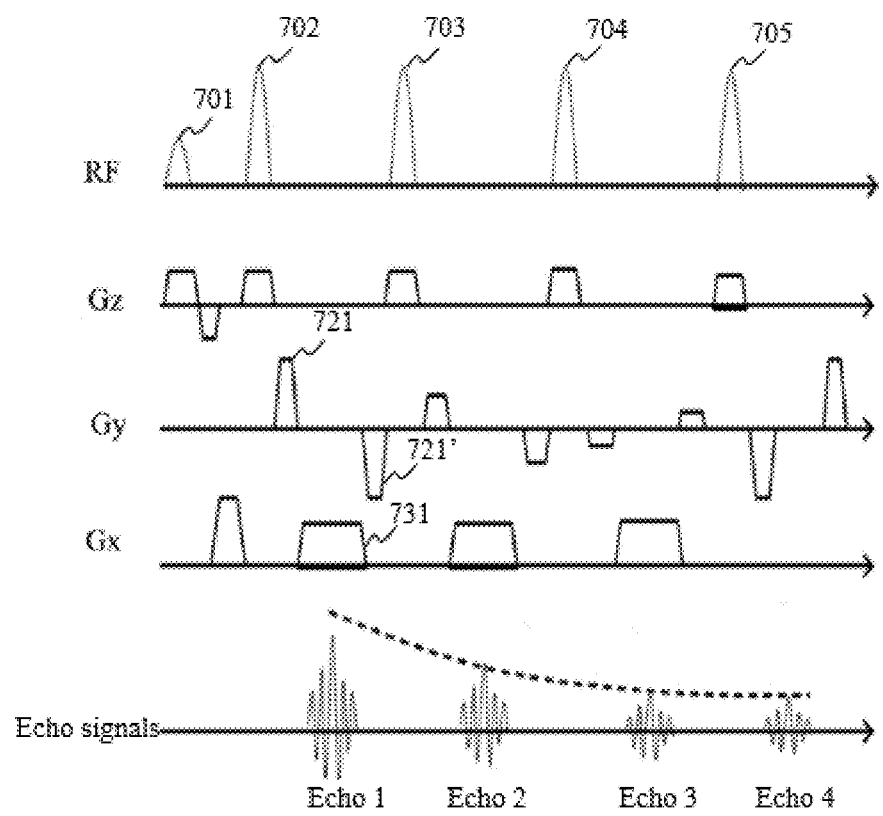
FIG. 7 shows an exemplary diagram of a FSE sequence in a single repetition time (TR) according to some embodiments of the present disclosure.

FIG. 7 shows an exemplary diagram of a FSE sequence in a single repetition time (TR) according to some embodiments of the present disclosure. As used herein, the repetition time (TR) may refer to the time between the applications of two consecutive excitation RF pulses. The RF pulse may include an excitation RF pulse 701 and a plurality of refocusing RF pulses including a refocusing RF pulse 702, a refocusing RF pulse 703, a refocusing RF pulse 704, and a refocusing RF pulse 705. In some embodiments, the flip angle of the excitation RF pulse 701 may be 90°. The flip angle of the refocusing RF pulses (702, 703, 704, and 705) may be 180°. As used herein, the flip angle is the rotation of the net magnetization vector by a radio frequency pulse relative to the main magnetic field. In some embodiments, the flip angle of the excitation RF pulse may be the same as that of the refocusing RF pulses. For example, because of T2 relaxation, the intensity of each echo in one echo train may be different. As used herein, the T2 relaxation may refer to the progressive dephasing of spinning dipoles following the excitation RF pulse as seen in a spin echo sequence due to one or more tissue-specific characteristics. Merely by way of example, the echo train length (ETL) is 4; to decrease the differences among the echoes in a same echo train, the flip angles of the refocusing RF pulses may be set to be values less than or equal to 180°, such as 140°, 155°, 165°, 180°, respectively. As used herein, the echo train length may refer to the number of echoes acquired within a single repetition time. In some embodiments, the flip angles of the refocusing pulses 702, 703, 704, and 705 may be the same as or different from each other.

As shown in FIG. 7, Gz may represent the slice selection gradient. In some embodiments, the slice selection gradient may be imposed along an axis perpendicular to the plane of the desired slice, resulting in a linear variation of potential resonance frequencies in that direction; a tailored RF pulse may be applied, of which the frequency components may match the range of frequencies contained in the desired slice. The combination of the slice selection gradient and the RF pulse may insure that the desired slice is excited. Following the excitation RF pulse 701, a plurality of refocusing RF pulses (702, 703, 704, and 705) may be transmitted to generate a plurality of echoes (e.g., echo 1, echo 2, echo 3, and echo 4). The number of echoes generated may be determined by the number of refocusing RF pulses. As illustrated in FIG. 7, the echo 1 may be generated by the refocusing RF pulse 702, the echo 2 may be generated by the refocusing RF pulse 703, the echo 3 may be generated by the refocusing RF pulse 704, and the echo 4 may be generated by the refocusing RF pulse 705. In some embodiments, Gx may represent the frequency encoding gradient, and Gy may represent the phase encoding gradient. The frequency encoding gradient and the phase encoding gradient may be used to spatially encode the echoes. For example, before the acquisition of the echo 1, the phase encoding gradient 721 may be applied. The phase encoding gradient 721' may be applied to adjust the echo 1 when the acquisition of echo 1 is complete. For example, the phase encoding gradient 721' may be used to eliminate the effects caused by the phase encoding gradient 721. During the acquisition of the echo 1, the frequency encoding gradient 731 may be applied. With the frequency encoding gradient and the phase encoding gradient, the echo 1 may be spatially encoded. A spatially encoded echo may correspond to a k-space trajectory and may be used to perform k-space sampling and construct MR images subsequently. According to the encoding gradients in FIG. 7, a Cartesian trajectory may be generated.

As shown in FIG. 7, each echo in an echo train may be acquired with a different echo time (TE). As used herein, an echo train may refer to a plurality of echoes generated in a single repetition time. As used herein, the echo time (TE) may refer to the time from the center of the first RF pulse (e.g., the excitation RF pulse) in a single repetition time to the center of the echo. FIG. 7 shows that, within a single repetition time, the echo time of the echo 1 may be shortest, while the echo time of the echo 4 may be longest. In some embodiments, the echoes filled into the center of the k-space may affect the image contrast and final image quality. The time between the middle of an excitation RF pulse and the middle of the echoes filled into the center of the k-space may be referred to as effective echo time (effective TE, or TEeff). In some embodiments, by adjusting the phase encoding gradient, any one of the echoes in the echo train may be filled into the center of the k-space.

In some embodiments, because of T2 relaxation, the signal intensity of each echo of an echo train may be different. As shown in FIG. 7, within a TR, the signal intensity of the echo 1 may be strongest, and while the signal intensity of the echo 4 may be weakest. According to the dash line shown in FIG. 7, the differences between the two adjacent echoes within a TR may diminish along with time. In some embodiments, the difference between the two adjacent echoes may be decreased by adjusting the flip angle of the refocusing RF pulse.

It should be noted that the above description about encoding gradients is merely provided for the purposes of illustration, and not intended to limit the scope of the present disclosure. For persons having ordinary skills in the art, multiple variations and modifications may be made under the teaching of the present invention. There may be different trajectories and different filling orders by adjusting the frequency encoding gradient and the phase encoding gradient. For example, in some embodiments, when an echo is being acquired, both of the frequency gradient and the phase gradient may be applied to generate a non-Cartesian k-space trajectory. The non-Cartesian trajectory may be radial, spiral, zigzag, propeller, or the like, or any combination thereof. However, those variations and modifications do not depart from the scope of the present disclosure.

FIG. 8-A shows an exemplary diagram of a k-space filling model for an FSE sequence as known in the prior art. As shown in FIG. 8-A, kx may represent the frequency encoding direction, ky may represent the phase encoding direction. In the k-space filling model illustrated in FIG. 8-A, L echoes may be generated in a single repetition time, and the k-space may be divided into L regions, including region 1, region 2, . . . , region L. N echoes may be filled into each region (for brevity, 1, 2, 3, . . . , N as illustrated). In each region, the number of the phase encoding lines may be N, and the total number of the phase encoding lines may be S. The mathematical relationship of N and S may be expressed as N=S/L. As illustrated in FIG. 8-A, i may represent the serial number of the echo train which the acquired echo is belong to; the same i may represent that the acquired echoes are from the same echo train. As shown in FIG. 8-A, during the filling process, echoes from the same echo train may be filled into different regions. For instance, echoes from the echo train 1 are filled into the region 1, region 2, . . . , region L respectively. As shown in FIG. 8-A, during the filling process, echoes from different echo trains but in the same position of each echo train may be filled into the same region. For instance, the nth echo from the echo train 1, the nth echo from the echo train 2, . . . , the nth echo from the echo train N, or the like, may be filled into a same region (e.g., the region 1).

As exemplified in FIG. 8-B, the ETL of the echo train may be 4, and the k-space may be divided into 4 regions. As illustrated, the phase encoding lines may be indicated by the lines filled with different colors (e.g., black, grey, or the like). The lines filled with a same color may be in different regions, while the lines filled with different colors may be in a same region. Echoes from the same echo train may be filled in the positions of the phase encoding lines with a same color. Mere by way of example, the echoes including echo 1, echo 2, echo 3, and echo 4 from the same echo train may be filled into the phase encoding lines with the black color. Echoes from different echo trains but located in a same position of the echo train may be filled into a same region. Merely by way of example, the size of the k-space may be set as 128×128. A first echo train may include echo 1, echo 2, echo 3, and echo 4, and the four echoes may be filled into the positions of which the phase encoding lines (ky) may be −128, −64, 0, 64, respectively. A second echo train may include echo 1', echo 2', echo 3', and echo 4', and the four echoes may be filled into the positions of which the phase encoding lines (ky) may be −127, −63, 1, 65, respectively. Other echoes of echo trains may be filled into the regions in the same way.

FIG. 9-A and FIG. 9-B show an exemplary diagram of a method of dividing the k-space according to some embodiments of the present disclosure. As illustrated, kx may represent the frequency encoding direction and ky may represent the phase encoding direction. As shown in FIG. 9-B, the k-space may be divided into a plurality of regions including region 1, region 2, . . . , region N−1, and region N. The upper diagram of FIG. 9-A may represent two regions of the k-space, and i and i+1 may represent the serial numbers of the regions. In some embodiments, the k-space may be divided into a plurality of regions just like region i and region i+1 along a dividing direction. If the k-space is two-dimensional, the dividing direction may be the phase encoding direction. If the k-space is three-dimensional, the dividing direction may be the first phase encoding direction, the second phase encoding direction, or the direction that is any linear combination of the first phase encoding direction and the second phase encoding direction. In the embodiment illustrated in FIG. 9-A, the k-space may be divided into a plurality of regions along the dividing direction (e.g., the phase encoding direction). As shown in the upper diagram of FIG. 9-A, the region with backward slashes within the region i and the region with backward slashes within the region i+1 may overlap (may be defined as an "overlapping region"). Similarly, the region with forward slashes within the region i+1, and the region with forward slashes within the region i+2 (not shown in FIG. 9-A) may overlap, and the region with forward slashes within the region i−1 (not shown in FIG. 9A), and the region with forward slashes within the region i may overlap. Further similarly, a plurality of overlapping regions may occur between two adjacent regions of the k-space.

In some embodiments, the size of the region may be fixed or variable. The sizes of the regions may be the same or different with each other. In some embodiments, the sizes of the regions may be set by the default of the system, or set by a user (e.g., an operator) based on one or more related parameters (e.g., number of the echoes of an echo line generated by the FSE sequence, contrast requirement of the final image, or the like, or a combination thereof). For example, the sizes of the regions may be set as increasing or decreasing in order (e.g., the size of region 2 may be larger than that of region 1, or the size of region 2 may be smaller than that of region 1). As another example, the sizes of the regions near the center of the k-space may be smaller than that of the regions far away from the center of the k-space. As a further example, the sizes of the regions may be symmetrical with respect to the center of the k-space. In some embodiments, the size of the overlapping region may be fixed or variable. The sizes of the overlapping regions may be the same or different with each other. For example, in one region, the two overlapping regions may be symmetrical or unsymmetrical with respect to the center axis of the region.

It should be noted that the above description is merely provided for the purposes of illustration, and not intended to limit the scope of the present disclosure. For persons having ordinary skills in the art, multiple variations and modifications may be made under the teaching of the present invention. For example, in some embodiments, the k-space may be derived from not only rectangular coordinate system but also non-rectangular coordinate systems, for example from polar coordinate system. The k-space may be divided into several regions along the radial direction. However, those variations and modifications do not depart from the scope of the present disclosure.

FIG. 10-A and FIG. 10-B show an exemplary diagram of a method of dividing the k-space according to some embodiments of the present disclosure. As illustrated in FIG. 10-A and FIG. 10-B, the k-space may be divided into a plurality of regions. The plurality of regions may include a first region including the center of the k-space (e.g., region B, region B') and a second region different from the first region. For example, the second region may be a region not including the center of the k-space. As another example, the second region may be a region including the center of the k-space but with a different size from the first region. In some embodiments, the second region may include a plurality of regions (e.g., region A, region C, region A', region C', or the like). In some embodiments, the k-space may be divided into a plurality of regions along a dividing direction. The dividing direction may be the first phase encoding direction, the second phase encoding direction, or any linear combination of the first phase encoding direction and the second phase encoding direction. In some embodiments, as shown in FIG. 10-A, in a rectangular coordinate system, the k-space may be divided along the phased encoding direction. In some embodiments, as shown in FIG. 10-B, in a polar coordinate system, the k-space may divided along the radial direction. In some embodiments, the plurality of regions may include a plurality of overlapping regions between any two adjacent regions (see FIGS. 9-A and 9-B). In some embodiments, as shown in FIG. 10-A and FIG. 10-B, the plurality of regions may be continuous with no overlapping regions.

Figure 11:
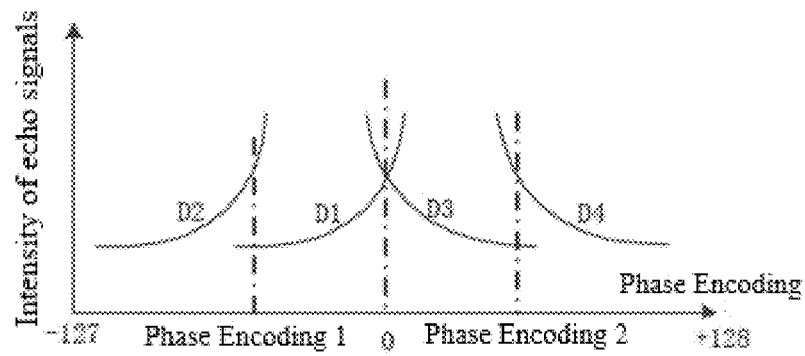
FIG. 11 illustrates filling data lines into the k-space according to some embodiments of the present disclosure.

FIG. 11 provides a schematic diagram illustrating filling data lines into the k-space according to some embodiments of the present disclosure. The X-axis represents phase encoding direction, and the range of the phase encoding direction may be [−127, 128] as shown in FIG. 11. The Y-axis represents the intensity of the echo signals. In some embodiments, a plurality groups of data lines (also called "echo line") may be filled into the k-space. As used herein, a group of data lines may include a plurality of data lines, and a data line may include a plurality of echoes (or "echo signals", see FIG. 7). The group of data lines may be acquired continuously by a single FSE sequence. As used herein, during an acquisition process, a group of data lines may be acquired by the single FSE sequence and filled into a region of the k-space (e.g., the region B including the center of the k-space illustrated in FIG. 10-A) along a filling direction (e.g., a filling direction described in FIG. 13-A or a filling direction described in FIG. 13-B). In some embodiments, for the plurality of groups of data lines, the number of the data lines in one group of data lines may be the same with that of the data lines in any other group of data lines. As shown in FIG. 9-A through FIG. 10-B, the k-space may be divided into a plurality of regions, including region 1, region 2, . . . , region N−1 and region N. In some embodiments, one region may correspond to one FSE sequence, and a group of data lines generated by one FSE sequence may be filled into the region. For example, as shown in FIG. 11, a first group of data lines D1 generated by a first FSE sequence (not shown in FIG. 11) may be filled into the region 1. Similarly, a second group D2, a third group D3, and a fourth group D4 generated by a second FSE sequence, a third FSE sequence and a fourth FSE sequence, respectively, may be filled into the region 2, region 3, and region 4 respectively.

In some embodiments, the range of the phase encoding direction may be divided into two sections including [−127, 0] and [0, +128]. In the section [−127, 0], the groups of data lines may be filled into the regions along a first filling direction, e.g., along the phase encoding direction or along the direction opposite to the phase encoding direction. In the section [0, +128], the groups of data lines may be filled into the regions along a second filling direction that is opposite to the first filling direction. For example, as illustrated, the filling directions of the first group D1 and the second group D2 may be the same. In some embodiments, the number of the data lines in the first group D1 may be the same or different from that in the second group D2. In some embodiments, there may be a mathematical relationship between the number of the data lines in the first group D1 and that in the second group D2. In some embodiments, two adjacent regions may include an overlapping region (see FIG. 9-A and FIG. 9-B). The groups of data lines filled into the adjacent regions may include one or more overlapping data lines. For example, the first group D1 and the second group D2 may include at least one overlapping data line along a same filling direction (e.g., phase encoding 1). As another example, the third group D3 and the fourth group D4 may also include at least one overlapping data line along a same filling direction (e.g., phase encoding 2). Similarly, other groups of data lines may be filled into the other regions of the k-space in the same way.

As is known, in a region near the center of the k-space (ky=0), the phase encoding gradient is low and from the center to the two end points (e.g., ky=−127 or ky=+128 in the case that the range of the k-space along the phase encoding direction is [−127, 128]), the phase encoding gradient increases gradually. The intensity of the echo signal may attenuate with the increase of the phase encoding gradient. In the region near the center of the k-pace, the intensity of the echo signals may be high and the signals may impact the final image contrast or image quality. In some embodiments, as shown in FIG. 11, the first group of data lines D1 and the third group of data lines D3 are filled into the regions near the center of k-space. The filling direction of the first group D1 is opposite to that of the third group D3, and the two groups may include at least an overlapping data line (e.g., the zero-phase encoding (ky=0)).

In some embodiments, at least three groups of data lines may be generated by N FSE sequences. Among the three groups of data lines, at least two groups of data lines may include the data line of which the phase encoding is the zero-phase encoding (the center of the k-space (ky=0)), at least one group of data lines of which the phase encoding is larger or smaller than the zero-phase encoding. For example, if N=3, two groups of data lines may include the data line of which the phase encoding direction is the zero-phase encoding, and one group of data lines of which the phase encoding is larger or smaller than the zero-phase encoding. As another example, if N=4, two groups of data lines may include the data line of which the phase encoding direction is the zero-phase encoding, and the other two groups of data lines of which the phase encoding is larger or smaller than the zero-phase encoding.

In some embodiments, for the data lines filled in the overlapping regions, a correction may be performed. For example, for the overlapping region between region 1 and region 2, the correction may be performed according to Equation (1) and Equation (2) below:

$$A = A1 + A2, \quad \text{Equation (1)}$$

and $$\varphi = \varphi 1 + \varphi 2, \quad \text{Equation (2)}$$

where A refers to the amplitude of echoes in the overlapping region, A1 refers to the amplitude of the echoes from region 1 filled into the overlapping region, A2 refers to the amplitude of the echoes from region 2 filled into the overlapping region, φ refers to the phase value of the echoes in the overlapping region, φ1 refers to the phase value of the echoes from region 1 filled into the overlapping region, φ2 refers to the phase value of the echoes from region 2 filled into the overlapping region.

As another example, the correction may be performed according to Equation (3) and Equation (4) below:

$$A = A1, \quad \text{Equation (3)}$$

and $$\varphi = \varphi 1. \quad \text{Equation (4)}$$

As a further example, the correction may be performed according to Equation (5) and Equation (6) below:

$$A = A2, \quad \text{Equation (5)}$$

and $$\varphi = \varphi 2. \quad \text{Equation (6)}$$

As a still further example, the correction may be performed according to Equation (7) and Equation (8) below:

$$A = \alpha 1 \times A1 + \alpha 2 \times A2, \quad \text{Equation (7)}$$

and $$\varphi = \alpha 1 \times \varphi 1 + \alpha 2 \times \varphi 2. \quad \text{Equation (8)}$$

As used herein, $\alpha 1$ and $\alpha 2$ refer to the weighting coefficients of A1 and A2 respectively, and $\alpha 1 + \alpha 2 = 1$, $0 \le \alpha 1$, $0 \le \alpha 2 \le 1$. In some embodiments, the weighting coefficients $\alpha 1$ and $\alpha 2$ may be determined using Equation (9) and Equation (10) below:

$$\alpha = 0.75 - 0.25 \times \cos\left(\frac{x-x_0}{x_0}\right) \times \pi, \quad \text{Equation (9)}$$

and $$\alpha = 0.25 + 0.25 \times \cos\left(\frac{x-x_0}{x_0}\right) \times \pi, \quad \text{Equation (10)}$$

As used herein, the direction pointing from the overlapping region toward the non-overlapping region may be defined as the positive direction, and the connection point of the overlapping region and the non-overlapping region may be defined as the origin of coordinates. In Equations (9) and (10), x0 refers to the x-coordinate of the center of the overlapping region, x refers to the x-coordinate of the overlapping region, a represents a weighting coefficient and α1=α.

In some embodiments, for an echo signal filled into the overlapping region, the weighting coefficient may be inversely proportional to the distance between the echo signal and the central axis of the region. The smaller the distance between the echo signal and the central axis of the region is, the larger the weighting coefficient may be, e.g., the closer to 1 the weighting coefficient may be; while the larger the distance between the echo signal and the central axis of the region is, the smaller the weighting coefficient may be, e.g., the closer to 0 the weighting coefficient may be.

This description is intended to be illustrative, and not to limit the scope of the present disclosure. Many alternatives, modifications, and variations will be apparent to those skilled in the art. The features, methods, and other characteristics of the exemplary embodiments described herein may be combined in various ways to obtain additional and/or alternative exemplary embodiments. For example, the value of N is not specific and may be adjusted under different situations. As another example, the overlapping region between the adjacent regions is not necessary, thus the overlapping data lines are not necessary.

Figure 12:
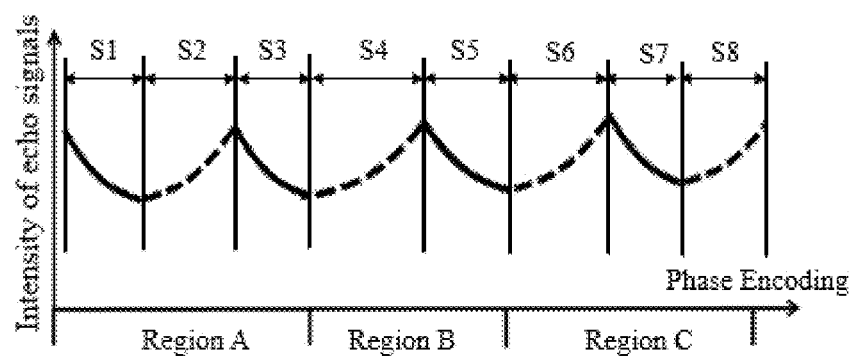
FIG. 12 illustrates filling data lines into the k-space according to some embodiments of the present disclosure.

FIG. 12 provides another schematic diagram illustrating filling data lines into the k-space according to some embodiments of the present disclosure. As shown in FIG. 10-A and FIG. 10-B, the k-space may be divided into a first region including the center of the k-space (e.g., region B, region B') and a second region different from the first region (e.g., region A, region C, region A', region C', or the like). As shown in FIG. 12, a plurality groups of data lines generated by a plurality of FSE sequences may be filled into the regions. In some embodiments, the first region (e.g., region B) and/or the second region (e.g., region A, or region C) may be divided into one or more segments (also referred to as "portion"). In some embodiments, one segment may correspond to one group of data lines. For example, as shown in FIG. 12, region A may be divided into segment S1, segment S2, and segment S3. Region B may be divided into segment S4 and segment S5. Region C may be divided into segment S6, segment S7, and segment S8. In some embodiments, the filling direction of at least a segment of the first region may be opposite to the filling direction of at least a portion of the second region. For example, the filling direction of segment S5 in region B is opposite to the filling direction of segment S6 in region C. In some embodiments, the filling direction of two adjacent segments may be opposite in order to avoid a sudden jump of data points (details may be found in, for example, FIG. 15-A and FIG. 15-B). As used herein, the phrase "two adjacent segments" may represent that one segment abuts the other segment. For example, as shown in FIG. 12, the filling directions of segment S1 and segment S2 in region A may be opposite.

FIG. 13-A and FIG. 13-B provide schematic diagrams illustrating filling echoes into the k-space according to some embodiments of the present disclosure. As illustrated, an echo line (also referred to as "data line" or "echo train") may include a plurality of echoes, e.g., echo #1, echo #2, echo #3, echo #4, and echo #5. For brevity, as used herein, echo #1 may refer to an echo of which the echo time may be shortest, and echo #5 may refer to an echo of which the echo time may be longest. In some embodiments, a FSE sequence may generate a group of echo lines, and each echo line may include a plurality of echoes including, for example, echo #1, echo #2, echo #3, echo #4, and echo #5. The groups of echo lines generated from a plurality of FSE sequences may be filled into the regions of the k-space along the filling direction (e.g., the phase encoding direction) as illustrated in FIG. 13-A, or along the direction opposite to the filling direction (e.g., the phase encoding direction) as illustrated in FIG. 13-B.

FIG. 14-A and FIG. 14-B illustrate the filling of echoes into a region near the center of the k-space according to some embodiments of the present disclosure. For the first region including the center of the k-space, in some embodiments, only one group of echo lines (also called "data line") may be filled into the first region in the way that illustrated in FIG. 13-A or FIG. 13-B.

The group of echo lines may be generated by one FSE sequence and may be filled into the first region near the center of k-space continuously along the filling direction (e.g., the phase encoding direction) or along the direction opposite to the filling direction (e.g., the phase encoding direction). In some embodiments, more than one group of echo lines may be filled into the first region, that is, echo lines from different FSE sequences may be filled into the first region. In some embodiments, if the echo with the effective TE (descriptions regarding effective TE may be found in FIG. 7) occurs at the beginning or the end of the echo line, the echoes of an echo line may be filled into the first region in the way illustrated in FIG. 14-A. As illustrated, the filled dots represent a first group of echo lines of which each echo line includes echo #1, echo #2, echo #3, echo #4 and echo #5, while the open dots represent a second group of echo lines of which each echo line includes echo #1', echo #2', echo #3', echo #4' and echo #5'. As shown in FIG. 14-A, the first region may be divided into two segments including a first segment and a second segment, the first group of echo lines may be filled into the first segment along the filling direction (e.g., the phase encoding direction), and the second group of echo lines may be filled into the second segment along the direction opposite to the filling direction (e.g., the phase encoding direction). The two groups of echo lines may be symmetrical relative to the center of the k-space.

In some embodiments, if the echo with the effective TE does not occur at the beginning or the end of the echo line, however for example, is set as the second echo of the echo line (e.g., echo #2 and echo #2') as illustrated in FIG. 14-B. The first group of echo lines may be filled into the first region along the filling direction (e.g., the phase encoding direction). The second group of echo lines may be filled into the first region along the direction opposite to the filling direction (e.g., the phase encoding direction). Because that the echoes with effective TE occur as the echo #2 and echo #2' and are filled near the center of the k-space, during the filling process, an overlapping part between the first group of echo lines and the second group of echo lines near the center of k-space may form. Echo #1 of the first group of echo lines may overlap with echo #3' of the second group of echo lines. Similarly, echo #1' of the second group of echo lines may overlap with echo #3 of the first group of echo lines. The filled echoes may be symmetrical relative to the center of k-space. Regarding the overlapping part between the first group of echo lines and the second group of echo lines, further data processing (e.g., a weighted averaging process) may be performed.

This description is intended to be illustrative, and not to limit the scope of the present disclosure. Many alternatives, modifications, and variations will be apparent to those skilled in the art. The features, methods, and other characteristics of the exemplary embodiments described herein may be combined in various ways to obtain additional and/or alternative exemplary embodiments. For example, see FIG. 14-B, the overlapping part between the first group and the second group is not necessary. The overlapping echoes (e.g., echo #1 of the first group of data lines and echo #3' of the second group of data lines) may be filled in an adjacent position with each other. In this embodiment, any further data processing is not necessary. As another example, the echoes with effective TE may be set as any echo of the echo lines, such as echo #3, echo #4, or the like.

FIG. 15-A and FIG. 15-B illustrate the filling of echoes into the region not including the center of the k-space according to some embodiments of the present disclosure. As illustrated, the second region not including the center of the k-space may be divided into a plurality of segments, including segment 1, segment 2, or the like. In some embodiments, the plurality of segments may include at least two adjacent segments, for example, segment 1 and segment 2. As shown in FIG. 15-A, in segment 1, the echo lines are filled along the direction opposite to the filling direction (e.g., the phase encoding direction), while in segment 2, the echo lines are filled along the filling direction (e.g., the phase encoding direction). For brevity, two echo lines are filled into segment 1 or segment 2, it should be noted that more than two echo lines may be filled into the segments. For other adjacent segments, echo lines may be filled in the same way to avoid jump of data points and keep the filled data smoothly.

In some embodiments, the adjacent segments may include an overlapping portion (see FIG. 9-A and FIG. 9-B). The echo lines may be filled into the adjacent segments along a same direction (e.g., the phase encoding direction or the direction opposite to the phase encoding direction). For the overlapping portion, some overlapping echoes or some overlapping parts of data lines may occur. The overlapping echoes or the parts of data lines may be further processed (e.g., a weighting process according to, for example, Equations (1)-(10)).

FIG. 16-A and FIG. 16-B are exemplary schematic diagrams of correcting the data filled into the k-space according to some embodiments of the present disclosure. As illustrated, region B may refer to the region including the center of the k-space, while region A and region C may refer to the regions not including the center of the k-space. The first set of data lines (or referred to as "echo line" or "echo train") marked with ① may be filled into the regions. The solid line may refer to a group of data lines that is filled into the region along the filling direction (e.g., the phase encoding direction), while the dashed line may refer to a group of data lines that is filled into the region along the direction opposite to the filling direction (e.g., opposite to the phase encoding direction). Intensity attenuation may occur along the data lines. The second set of data lines marked with ② may be filled into the regions of the k-space along a filling direction that is opposite to that of the set marked with ①. It means that at any point of the phase encoding, the filled echo signals may be repeatedly acquired (e.g., at least twice), and a mathematical processing, e.g., a weighted averaging process, may be performed regarding the echo signals.

As illustrated in FIG. 16-B, for a portion (also referred to as a "segment") of a region (see, for example, FIG. 12), suppose that the echoes may be filled into the k-space along the phase encoding direction. As used herein, the region may include the region B, the region A, the region C, or any region divided from the k-space. As used herein, a portion of the region may refer to a portion in which a group of data lines may be filled (see details in FIG. 12). As illustrated in FIG. 16-B, the phase encoding range of the portion may be $PE_1 \sim PE_{ETL}$, and a group of data lines may be filled in the portion. For brevity, only a first data line (also referred to as an "echo train") including echo 1, echo 2, . . . , echo x, . . . , echo ETL filled into the portion along the phase encoding direction is shown. For a phase encoding site PEx in the portion, an echo x may be filled in the phase encoding site. In some embodiments, a second data line including echo 1', echo 2', . . . , echo y, . . . , echo ETL' may be filled into the portion along the direction opposite to the phase encoding direction. As illustrated, an echo y may be filled in the phase encoding site PEx. As used herein, y=ETL-x+1, 1≤x≤ETL, 1≤y≤ETL. A weighted averaging process may be performed on the echo x and echo y filled at the PEx site, and the effect of signal intensity attenuation on image quality may be reduced or eliminated.

This description is intended to be illustrative, and not to limit the scope of the present disclosure. Many alternatives, modifications, and variations will be apparent to those skilled in the art. The features, methods, and other characteristics of the exemplary embodiments described herein may be combined in various ways to obtain additional and/or alternative exemplary embodiments. For example, besides the phase encoding direction, the echoes may be filled into the k-space along any linear combination direction of the first and the second encoding directions (e.g., the radial orientation).

FIG. 17-A through FIG. 17-D illustrate four exemplary images produced by the data acquired from the abdomen with different image producing procedures according to some embodiments of the present disclosure. FIG. 17-A and FIG. 17-B show two images of the abdomen (fat saturation) produced by the data that was filled into the k-space by a traditional method and by the filling method disclosed in the present disclosure respectively. FIG. 17-C and FIG. 17-D show two images of the abdomen (no fat saturation) produced by the data that were filled into the k-space by the traditional method and by the filling method disclosed in the present disclosure respectively. As shown in FIG. 17-A and FIG. 17-C, The images of the abdomen produced by the data that were filled into the k-space by the traditional method had some defects or artifacts because of the breath interference of the subject being scanned. For example, the imaging of the liver area was not clear, and it was difficult to identify the vascular profile. During the process for obtaining the images shown in FIG. 17-B and FIG. 17-D, the k-space was divided into a plurality of regions, among which two adjacent regions include an overlapping region (see FIG. 9-A and FIG. 9-B). In the overlapping region, a weighted averaging process was performed on the filled data. It may be seen that the structures of the abdominal area and the liver area were clear, the details were clearly visible, the vascular profile was improved, and the artifacts of the bright band on the border were almost invisible. The image producing procedure disclosed in the present disclosure may be effective in reducing signal abnormalities caused by breathing, and decreasing the sensitivity of image quality to motion, regardless of with or without fat saturation.

FIG. 18-A and FIG. 18-B show two images of the neck produced by the data that is filled into the k-space by a traditional method described in FIG. 8-A and FIG. 8-B and by the filling method disclosed in the present disclosure respectively. As shown in FIG. 18-A, the image produced by the data that was filled into the k-space by the traditional method had obvious cerebrospinal fluid (CSF) pulsation artifacts. As shown in FIG. 18-B, during the process for obtaining the image, the k-space was divided into a plurality of regions including a first region including the center of the k-space and a second region different form the first region (see FIG. 10-A and FIG. 10-B). It may be seen that the CSF pulsation artifact was significantly reduced, and meanwhile the clarity of the structure of the intervertebral disc was improved. The image producing procedures in the present disclosure may be effective in reducing artifacts induced by the periodic motion of CSF.

It should be noted that the above description is merely provided for the purposes of illustration, and not intended to limit the scope of the present disclosure. The image producing procedures in the present disclosure may be effective in reducing, removing or eliminating other types of motion artifacts including, for example, the vascular pulsation, heart movement, and random motion of the subject being scanned, or the like, or any combination thereof.

The image producing procedures in the present disclosure may be applied to whole body MR imaging, and the images produced may have more clear structural details.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languges, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities of ingredients, properties such as molecular weight, reaction conditions, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on a computing device having at least one processor and at least one storage medium, the method comprising:
    dividing k-space into a plurality of regions along a dividing direction, the plurality of regions comprising a first region including a center of the k-space and a second region adjacent to but different from the first region, wherein the first region includes a first sub-region and a second sub-region, and the first sub-region and the second sub-region are symmetric with respect to the center of the k-space;
    acquiring a plurality of groups of data lines along the dividing direction by scanning an object using a plurality of sampling sequences, each group of data lines corresponding to a respective one of the plurality of sampling sequences and filled into a respective one of the plurality of regions along a filling direction, the filling direction being along a phase encoding direction in magnetic resonance imaging or opposite to the phase encoding direction, wherein
        the filing direction of at least a portion of the first region is opposite to the filling direction of at least a portion of the second region, and
        the plurality of groups of data lines include a first group of data lines and a second group of data lines, the first group of data lines and the second group of data lines being symmetrically filled into the first sub-region and the second sub-region, respectively; and
    obtaining a magnetic resonance image of the object by reconstructing the plurality of groups of data lines filled into the k-space.

2. The method of claim 1, the first group of data lines and the second group of data lines partially overlapping with each other.

3. The method of claim 2, further comprising:
    performing a weighting averaging operation on an overlapping part of the first group of data lines and the second group of data lines.

4. The method of claim 1, the first region and the second region partially overlapping with each other.

5. The method of claim 4, further comprising:
    performing an amplitude correction or a phase correction on data lines filled into an overlapping area of the first region and the second region.

6. The method of claim 1,
    the second region including a first portion and a second portion,
    the first portion and the second portion being symmetric with respect to the center of the k-space,
    the first portion including a plurality of first segments,
    the second portion including a plurality of second segments, wherein each of the plurality of second segments corresponds to a respective one of the plurality of first segments with respect to the center of the k-space.

7. The method of claim 6,
    adjacent first segments of the plurality of first segments partially overlapping with each other; and
    adjacent second segments of the plurality of second segments partially overlapping with each other.

8. The method of claim 7, further comprising:
    performing an amplitude correction or a phase correction on data lines filled into an overlapping area of the adjacent first segments or the adjacent second segments.

9. The method of claim 6, wherein the plurality of groups of data lines include a third group of data lines and a fourth group of data lines, the third group of data lines and the fourth group of data lines being symmetrically filled into the first segment and the corresponding second segment.

10. The method of claim 6, wherein
    the filling directions of the plurality of first segments are the same, and
    the filling directions of the plurality of second segments are the same and opposite to the filling directions of the plurality of first segments.

11. The method of claim 6, wherein
    the filling directions of adjacent first segments are opposite to each other; or
    the filling directions of adjacent second segments are opposite to each other.

12. The method of claim 1, wherein each of the plurality of data lines includes a plurality of echo signals corresponding to a plurality of echo times respectively.

13. The method of claim 1, further comprising:
    acquiring a plurality of supplementary groups of data lines along the dividing direction by scanning the object using the plurality of sampling sequences, each supplementary group of data lines corresponding to a respective one of the plurality of sampling sequences and filled into a respective one of the plurality of regions along a direction opposite to the filling direction; and performing a weighted averaging operation on the plurality of group of data lines and the plurality of supplementary groups of data lines.

14. A system, comprising:

a storage storing instructions;

a processor in communication with the storage, wherein when executing the instructions, the processor is caused to:

divide k space into a plurality of regions along a dividing direction, the plurality of regions comprising a first region including a center of the k-space and a second region adjacent to but different from the first region, wherein the first region includes a first sub-region and a second sub-region, and the first sub-region and the second sub-region are symmetric with respect to the center of the k-space;

acquire a plurality of groups of data lines along the dividing direction by scanning an object using a plurality of sampling sequences, each group of data lines corresponding to a respective one of the plurality of sampling sequences and filled into a respective one of the plurality of regions along a filling direction the filling direction being along a phase encoding direction in magnetic resonance imaging or opposite to the phase encoding direction, wherein the filing direction of at least a portion of the first region is opposite to the filling direction of at least a portion of the second region, and the plurality of groups of data lines include a first group of data lines and a second group of data lines, the first group of data lines and the second group of data lines being symmetrically filled into the first sub-region and the second sub-region, respectively; and obtain a magnetic resonance image of the object by reconstructing the plurality of groups of data lines filled into the k-space.

15. The system of claim 14, the first group of data lines and the second group of data lines partially overlapping with each other.

16. The system of claim 14, the first region and the second region partially overlapping with each other.

17. The system of claim 14, the second region including a first portion and a second portion, the first portion and the second portion being symmetric with respect to the center of the k-space, the first portion including a plurality of first segments, the second portion including a plurality of second segments, wherein each of the plurality of second segments corresponds to a respective one of the plurality of first segments with respect to the center of the k-space.

18. The system of claim 17, adjacent first segments of the plurality of first segments partially overlapping with each other; and adjacent second segments of the plurality of second segments partially overlapping with each other.

19. The system of claim 17, wherein the plurality of groups of data lines include a third group of data lines and a fourth group of data lines, the third group of data lines and the fourth group of data lines being symmetrically filled into the first segment and the corresponding second segment.

20. The system of claim 17, wherein the filling directions of the plurality of first segments are the same, and the filling directions of the plurality of second segments are the same and opposite to the filling directions of the plurality of first segments.

* * * * *